United States Patent
Kimura et al.

(10) Patent No.: US 10,586,354 B2
(45) Date of Patent: Mar. 10, 2020

(54) IMAGING METHOD AND IMAGING APPARATUS

(71) Applicants: National University Corporation Kobe University, Hyogo (JP); Integral Geometry Science Inc., Hyogo (JP)

(72) Inventors: Kenjiro Kimura, Hyogo (JP); Noriaki Kimura, Hyogo (JP)

(73) Assignees: NATIONAL UNIVERSITY CORPORATION KOBE UNIVERSITY, Hyogo (JP); INTEGRAL GEOMETRY SCIENCE INC., Hyogo (JP)

( * ) Notice: Subject to any disclaimer, the term of this patent is extended or adjusted under 35 U.S.C. 154(b) by 66 days.

(21) Appl. No.: 15/764,091

(22) PCT Filed: Sep. 28, 2016

(86) PCT No.: PCT/JP2016/078742
§ 371 (c)(1),
(2) Date: Mar. 28, 2018

(87) PCT Pub. No.: WO2017/057524
PCT Pub. Date: Apr. 6, 2017

(65) Prior Publication Data
US 2018/0308259 A1    Oct. 25, 2018

(30) Foreign Application Priority Data
Sep. 29, 2015  (JP) .................. 2015-192216

(51) Int. Cl.
*G06K 9/00*  (2006.01)
*G06T 11/00*  (2006.01)
(Continued)

(52) U.S. Cl.
CPC ............ *G06T 11/003* (2013.01); *A61B 6/032* (2013.01); *G06T 7/50* (2017.01); *H04N 19/172* (2014.11)

(58) Field of Classification Search
None
See application file for complete search history.

(56) References Cited

U.S. PATENT DOCUMENTS

2006/0247513 A1* 11/2006 Wang .................... A61B 6/032
                                                                                600/410
2013/0135136 A1    5/2013 Haynes et al.

FOREIGN PATENT DOCUMENTS

| CN | 102823062 | 12/2012 |
| JP | 2003-177656 | 6/2003 |
| WO | 2015/136936 | 9/2015 |

OTHER PUBLICATIONS

Extended European Search Report dated May 14, 2019 in European Patent Application No. 16851695.3.
(Continued)

*Primary Examiner* — Atiba O Fitzpatrick
(74) *Attorney, Agent, or Firm* — Wenderoth, Lind & Ponack, L.L.P.

(57) ABSTRACT

An imaging method includes a step of radiating a wave to a target object, a step of receiving a scattered wave as a result of the wave being scattered at the target object, and a step of reconstructing an image regarding internal information of the target object on the basis of scattered wave data indicating the scattered wave. In the step of reconstructing the image, a reconstruction function is derived by solving a partial differential equation by using the scattered wave data and an analysis model indicating a shape, and the image regarding the internal information of the target object is reconstructed by using the reconstruction function. Here, the partial differential equation is an equation satisfied by the
(Continued)

reconstruction function for reconstructing the image regarding the internal information of the target object.

20 Claims, 9 Drawing Sheets

(51) Int. Cl.
*H04N 19/172* (2014.01)
*G06T 7/50* (2017.01)
*A61B 6/03* (2006.01)

(56) References Cited

OTHER PUBLICATIONS

Emanuele Salerno, "Microwave Tomography of Lossy Objects from Monostatic Measurements", IEEE Transactions on Microwave Theory and Techniques, Jul. 1999, vol. 47, No. 7 pp. 986-994.
Burkholder et al., "Comparison of Monostatic and Bistatic Radar Images", IEEE Antennas and Propagation Magazine, Jun. 2003, vol. 45, No. 3, pp. 41-50.
International Search Report dated Dec. 6, 2016 in International (PCT) Application No. PCT/JP2016/078742.
Kazuaki Ezawa et al., "Development of the 3D Imaging Radar for Inspection of Tunnel Lining Concrete", Mitsui Engineering & Shipbuilding Technical Report, No. 184, pp. 24, Feb. 2005.
Office Action dated Dec. 19, 2019 in Chinese Application No. 201680059162.X, with partial English translation.
Dan Zhen Qing, "Sensors and detection technology vocational education five innovative planning materials", Beijing Institute of Technology Press, 197-198, 2013 (cited in Chinese Office Action).

* cited by examiner

IMAGING METHOD AND IMAGING APPARATUS

TECHNICAL FIELD

The present invention relates to a technique of acquiring and imaging internal information of an object by using waves, and, particularly to an imaging method and an imaging apparatus capable of acquiring internal information of an object by using a scattering phenomenon of waves.

BACKGROUND ART

In the related art, as a method of imaging internal information of an object such as a living body or a building, there is a method using X-ray computed tomography (X-ray CT), magnetic resonance imaging (MRI), or positron emission tomography (PET). Specifically, waves, for example, electromagnetic waves such as light, terahertz waves, millimeter waves, or microwaves, or ultrasonic waves are radiated to a living body, an object, or plasma which is an observation target object, scattered waves (reflected waves) thereof are observed and analyzed, and thus internal information of a living body, a solid, or plasma is imaged. In recent years, internal information of a living body or an object has been imaged by using magnetic fields instead of waves.

Generally, such a method employs a technique in which a wave u such as an electromagnetic wave or an ultrasonic wave is radiated to an object O, scattered waves p which are scattered from the object O at a plurality of locations around the object O are observed, and obtained data is imaged (for example, refer to Patent Document 1 and Non-Patent Document 1).

In the technique disclosed in Patent Document 1, internal information of an object is imaged by using an electric wave. Data is repeatedly acquired so as to be imaged while data regarding scattered waves observed by sensor elements disposed on a circumference is being corrected with parameters such as conductivity or permittivity.

The technique disclosed in Non-Patent Document 1 is a technique relating to a multi-path linear array radar, and is to image information regarding defects or the like of concrete. Sensor elements (linear multi-array antenna) which are arranged in a linear or curved shape are disposed on a surface of a target object, scattered waves of radiated waves are observed by the sensors, and observed data is imaged through analysis.

In a medical field, it is expected that an observation method using such waves is used for, for example, a mammography apparatus detecting a breast cancer.

RELATED DOCUMENT

Patent Document

[Patent Document 1] Japanese Laid-open Patent Publication No. 2003-177656

Non-Patent Document

[Non-Patent Document 1] Development of the 3D Imaging Radar for Inspection of Tunnel Lining Concrete, Mitsui Engineering & Shipbuilding Technical Report, No. 184, p 24, February 2005

SUMMARY OF THE INVENTION

Technical Problem

In the techniques disclosed in Patent Document 1 and Non-Patent Document 1, for example, whenever a condition such as a curved surface shape of an object is changed, data is acquired again or acquired data is corrected by changing theory or an internal structure of an apparatus, and thus the techniques are hard to versatilely use. Particularly, since, in a target object such as a living body having a flexible shape, a curvature of a shape or an outer appearance of the target object is often inconstant, it is hard to uniformly use the linear multi-array antenna of the related art or an array antenna with a target object having a constant shape as a model. Since data is required to be acquired again or to be corrected, there is a problem such as delay of a computation speed or use of a large memory volume.

Regarding the related art in a case where a target object is a living body, there is an apparatus such as a mammography apparatus using X-rays. However, in the mammography apparatus using X-rays, particularly, with respect to high-density breasts occupying the majority of Asians, a cancer may be indirectly diagnosed by imaging calcium carbonate, and thus it is difficult to directly identify minute breast cancer tissue from other tissues.

In recent years, a method using scattering of high-luminance X-rays has been proposed, but scattered light with the intensity of one several millionths of that of transmitted light is measured, and thus it is necessary to increase the intensity of X-rays in order to perform accurate diagnosis. In this case, the influence of X-rays exerted on a living body is concerned.

Therefore, an object of the present invention is to provide an examination method and an examination apparatus which can versatilely image internal information of an object easily and at a high speed.

Solution to Problem

In order to solve the problem, according to the present invention, there is provided an imaging method including
a step of radiating a wave to a target object;
a step of receiving a scattered wave as a result of the wave being scattered at the target object; and
a step of reconstructing an image regarding internal information of the target object on the basis of scattered wave data indicating the scattered wave,
in which, in the step of reconstructing the image,
a reconstruction function for reconstructing the image regarding the internal information of the target object is derived by solving a partial differential equation by using the scattered wave data and an analysis model indicating a shape, and
the image regarding the internal information of the target object is reconstructed by using the reconstruction function, and
in which the partial differential equation is an equation satisfied by the reconstruction function.

Consequently, in the analysis model in which observation (examination) of internal information of a target object is performed while the sensor element including the transmitting antenna element and the receiving antenna element is being freely moved on the target object, a partial differential equation for inverse problem is set, and the internal information of the target object can be imaged versatilely and at a high speed by solving the equation. In the step of reconstructing an image, the reconstruction function ϕ is set in a three-dimensional space, and thus it is possible to image internal information of the target object with high accuracy and at a high speed in three dimensions. The target object can be directly observed instead of observing the target object by using an observation result of another object.

When compared with an examination apparatus using scattering tomography according to a multistatic method including a plurality of transmitting units and receiving units, this examination method is an examination method using scattering tomography according to a monostatic method, and it is possible to measure even an examination target having a flexible shape with high accuracy.

The partial differential equation may be expressed by using independent variables indicating positions of a transmitting point and a receiving point in the target object, and a linear partial differential equation having, as a solution, a scattering field function which is a function of a location where the scattered wave is generated at each point in a space having the same order as the number of the independent variables, and, in the step of reconstructing the image, an imaging function which is a limiting value of a time variable of the reconstruction function may be derived, and the image regarding the internal information of the target object may be reconstructed by using the imaging function.

Consequently, it is possible to image internal information of a target object with higher accuracy and at a high speed.

The shape indicated by the analysis model may be a shape of a cone, the imaging function may be expressed by the following Equation (A), and, in the step of reconstructing the image, the image regarding the internal information of the target object may be reconstructed by using a function expressed by the following Equation (B) which is obtained by integrating the imaging function with θ.

[Math. 1]

$$\rho(x, y, z, \theta) = \int_{-\infty}^{\infty} \phi(x, y, z, k)dk \quad (A)$$
$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)$$
$$\left(\frac{dk}{dk_z}\right) dk_x dk_y dk_z$$

[Math. 2]

$$P(X, Y, Z) = \int_0^{2\pi} \rho(x, y, z, \theta)d\theta \quad (B)$$

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the cone is set to the origin, a direction directed from the origin toward the center of a base of the cone is set to a Z direction, a direction passing through the origin in parallel to the base is set to an X direction, and a direction passing through the origin in parallel to the base and orthogonal to the X direction is set to a Y direction; ρ is a function of permittivity; ϕ is the reconstruction function; $\phi_R$ is a function satisfying $\phi = \phi_R \delta$ (x); $k_x$, $k_y$, and $k_z$ are respectively x, y and z components of a wave number; k is a time wave number; and θ is a rotation angle with an axis of the cone as a rotation axis.

Consequently, it is possible to image internal information of a target object having an approximately conical shape with higher accuracy and at a high speed.

The shape indicated by the analysis model may be a shape of a substantial cone having a curved generating line, the imaging function may be expressed by the following Equation (C), and, in the step of reconstructing the image, the image regarding the internal information of the target object may be reconstructed by using a function expressed by the following Equation (D) which is obtained by integrating the imaging function with θ.

[Math. 3]

$$\rho(x, y, z, \theta) = \int_{-\infty}^{\infty} \phi(x, y, z, k)dk \quad (C)$$
$$= \int_{-\infty}^{\infty}\left[\frac{1}{(2\pi)^2}\int_{-\infty}^{\infty}\int_{-\infty}^{\infty} e^{-i(k_x x + k_y y)} a_\theta(k_x, k_y, k)\right.$$
$$\left. e^{iz\sqrt{4k^2 - k_x^2 - k_y^2}} dk_x dk_y \right] dk$$
$$= \frac{1}{(2\pi)^2}\int_{-\infty}^{\infty}\int_{-\infty}^{\infty}\int_{-\infty}^{\infty} e^{-i(k_x x + k_y y - k_z z)} a_\theta(k_x, k_y, k)$$
$$\left(\frac{dk}{dk_z}\right) dk_x dk_y dk_z$$

$$k_z = \sqrt{4k^2 - k_x^2 - k_y^2}$$

$$\frac{dk}{dk_z} = \frac{d}{dk_z}\left(\frac{1}{2}\sqrt{k_x^2 + k_y^2 + k_z^2}\right) = \frac{1}{2}\frac{k_z}{\sqrt{k_x^2 + k_y^2 + k_z^2}}$$

[Math. 4]

$$P(X, Y, Z) = \int_0^{2\pi} \rho(x, y, z, \theta)d\theta \quad (D)$$

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the substantial cone is set to the origin, a direction directed from the origin toward the center of a base of the substantial cone is set to a Z direction, a direction passing through the origin in parallel to the base is set to an X direction, and a direction passing through the origin in parallel to the base and orthogonal to the X direction is set to a Y direction; ρ is a function of permittivity; ϕ is the reconstruction function; $a_\theta$ is a coefficient; $k_x$, $k_y$, and $k_z$ are respectively x, y and z components of a wave number; k is a time wave number; and θ is a rotation angle with an axis of the substantial cone as a rotation axis.

Consequently, it is possible to image internal information of a target object having a substantially conical shape with higher accuracy and at a high speed.

The shape indicated by the analysis model may be a shape of an asymmetric pyramid, the imaging function may be expressed by the following Equation (F) in a case where each of, and is a variable satisfying the following Equation (E), and, in the step of reconstructing the image, the image regarding the internal information of the target object may be reconstructed by using a function expressed by the following Equation (G) which is obtained by integrating the imaging function with θ.

[Math. 5]

$$\xi = -k_x\cos\theta + \{k_y\cos\alpha(\theta) + k_z\sin\alpha(\theta)\}\sin\theta \quad (E)$$
$$\eta = -k_x\sin\theta - \{k_y\cos\alpha(\theta) + k_z\sin\alpha(\theta)\}\cos\theta$$
$$\zeta = -k_y\sin\alpha(\theta) + k_z\cos\alpha(\theta)$$
$$k_x = -\xi\cos\theta - \eta\sin\theta$$
$$k_y = (\xi\sin\theta - \eta\cos\theta)\cos\alpha(\theta) - \zeta\sin\alpha(\theta)$$
$$k_z = (\xi\sin\theta - \eta\cos\theta)\sin\alpha(\theta) + \zeta\cos\alpha(\theta)$$

[Math. 6]

$$\rho(x, y, z, \theta) = \quad (F)$$
$$\frac{1}{(2\pi)^2}\int_{-\infty}^{\infty}\int_{-\infty}^{\infty}\int_{-\infty}^{\infty}e^{i(\xi X+\eta Y+\zeta Z)}\tilde{\phi}_R(k_y, k, \theta)\left(\frac{dk}{dk_z}\right)d\xi d\eta d\zeta$$
$$k = \frac{1}{2}\sqrt{k_x^2 + k_y^2 + k_z^2} = \frac{1}{2}\sqrt{\xi^2 + \eta^2 + \zeta^2}$$
$$\frac{dk}{dk_z} = \frac{k_z}{2\sqrt{k_x^2 + k_y^2 + k_z^2}} = \frac{(\xi\sin\theta - \eta\cos\theta)\sin\alpha + \zeta\cos\alpha}{2\sqrt{\xi^2 + \eta^2 + \zeta^2}}$$

[Math. 7]

$$P(X, Y, Z) = \int_0^{2\pi}\rho(x, y, z, \theta)d\theta \quad (G)$$

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the pyramid is set to the origin, a direction directed from the origin toward the center of a base of the pyramid is set to a Z direction, a direction passing through the origin in parallel to the base is set to an X direction, and a direction passing through the origin in parallel to the base and orthogonal to the X direction is set to a Y direction; $\rho$ is a function of permittivity; $\phi$ is the reconstruction function; $\phi_R$ is a function satisfying $\phi=\phi_R\delta(x)$; $a_\theta$ is a coefficient; $k_x$, $k_y$, and $k_z$ are respectively x, y and z components of a wave number; k is a time wave number; $\theta$ is a rotation angle with an axis of the pyramid as a rotation axis; and $\alpha$ is an inclined angle with the Z direction as a reference.

Consequently, it is possible to image internal information of a target object having a substantially asymmetric pyramidal shape with higher accuracy and at a high speed.

In the radiating step, the wave may be radiated to the target object by using a probe in which a receiving antenna element receiving the scattered wave and a transmitting antenna element radiating the wave to the target object are integrally provided, and an electric wave absorbing portion is located between the receiving antenna element and the transmitting antenna element, and, in the receiving step, the scattered wave may be received by using the probe.

Consequently, it is possible to reduce the magnitude of a wave which is directly received by the receiving antenna element among waves transmitted from the transmitting antenna element, and thus to increase a ratio of the magnitude of a scattered wave from a target object received by the receiving antenna element to the magnitude of the wave directly received. Therefore, it is possible to obtain a clearer image of the inside of a target object.

The shape indicated by the analysis model may be a shape of a cone, and the transmitting antenna element and the receiving antenna element may be integrally moved along a line corresponding to a generating line of a cone in the target object.

Consequently, in an analysis model in which the sensor element is moved on a generating line of a cone, a partial differential equation for inverse problem is set, and internal information of a target object can be imaged versatilely and at a high speed by solving the equation. Particularly, it is possible to image internal information of a target object having a conical shape with higher accuracy and at a high speed.

The shape indicated by the analysis model may be a shape of a substantial cone having a curved generating line, and the transmitting antenna element and the receiving antenna element may be integrally moved along a line corresponding to a curved generating line of a substantial cone in the target object.

Consequently, in an analysis model in which the sensor element is moved on a curved generating line, a partial differential equation for inverse problem is set, and internal information of a target object can be imaged versatilely and at a high speed by solving the equation. Particularly, it is possible to image internal information of a target object having a substantially conical shape, for example, a hemispherical shape or a dome-like shape with higher accuracy and at a high speed.

The shape indicated by the analysis model may be a shape of an asymmetric pyramid, and the transmitting antenna element and the receiving antenna element may be integrally moved along a line corresponding to a generating line of an asymmetric pyramid in the target object.

Consequently, in an analysis model in which the sensor element is moved on a generating line of an asymmetric pyramidal shape, a partial differential equation for inverse problem is set, and internal information of a target object can be imaged versatilely and at a high speed by solving the equation. Particularly, it is possible to image internal information of a target object having a shape in which a part of a conical shape or a substantially conical shape is omitted, or a target object having a flexible shape with higher accuracy and at a high speed.

The wave may be a microwave.

Consequently, it is possible to image internal information of a target object according to a versatile and simple method regardless of an amount of water.

The wave may be a pulse wave or a periodic wave with a predetermined frequency.

Consequently, it is possible to image internal information of a target object having a flexible shape according to a versatile and simple method.

In order to solve the problem, according to the present invention, there is provided an imaging apparatus including a transmitting antenna element that radiates a wave to a target object;

a receiving antenna element that receives a scattered wave as a result of the wave radiated from the transmitting antenna element being scattered at the target object; and an image reconstruction unit that reconstructs an image regarding internal information of the target object on the basis of scattered wave data indicating the scattered wave received by the receiving antenna element, in which the image reconstruction unit derives a reconstruction function for reconstructing the image regarding the internal information of the target object by solving a partial differential equation by using the scattered wave data and an analysis model indicating a shape, and reconstructs the image regarding the internal information of the target object by using the reconstruction function, and in which the partial differential equation is an equation satisfied by the reconstruction function.

Consequently, in the analysis model in which observation (examination) of a target object is performed while the sensor element including the transmitting antenna element and the receiving antenna element is being freely moved on the target object, a partial differential equation for inverse problem is set, and the internal information of the target object can be imaged versatilely and at a high speed by solving the equation. In reconstructing an image, the reconstruction function ϕ is set in a three-dimensional space, and thus it is possible to image internal information of the target object with high accuracy and at a high speed in three dimensions. The target object can be directly observed instead of observing the target object by using an observation result of another object.

When compared with an examination apparatus using scattering tomography according to a multistatic method including a plurality of transmitting units and receiving units, this examination apparatus is an examination apparatus using scattering tomography according to a monostatic method, and it is possible to measure even an examination target having a flexible shape with high accuracy.

The partial differential equation may be expressed by using independent variables indicating positions of a transmitting point and a receiving point in the target object, and a linear partial differential equation having, as a solution, a scattering field function which is a function of a location where the scattered wave is generated at each point in a space having the same order as the number of the independent variables, and, the image reconstruction unit may derive an imaging function which is a limiting value of a time variable of the reconstruction function, and may reconstruct the image regarding the internal information of the target object by using the imaging function.

Consequently, it is possible to image internal information of a target object with higher accuracy and at a high speed.

The shape indicated by the analysis model may be a shape of a cone, the imaging function may be expressed by the following Equation (A), and, the image reconstruction unit may reconstruct the image regarding the internal information of the target object by using a function expressed by the following Equation (B) which is obtained by integrating the imaging function with θ.

[Math. 8]

$$\rho(x, y, z, \theta) = \int_{-\infty}^{\infty} \phi(x, y, z, k) dk \quad (A)$$
$$= \frac{1}{(2\pi)^2} \int_{-\infty}^{\infty} \int_{-\infty}^{\infty} \int_{-\infty}^{\infty} e^{-i(k_x x + k_y y)} e^{ik_z z} \tilde{\phi}_R(k_y, k, \theta)$$
$$\left(\frac{dk}{dk_z}\right) dk_x dk_y dk_z$$

[Math. 9]

$$P(X, Y, Z) = \int_0^{2\pi} \rho(x, y, z, \theta) d\theta \quad (B)$$

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the cone is set to the origin, a direction directed from the origin toward the center of a base of the cone is set to a Z direction, a direction passing through the origin in parallel to the base is set to an X direction, and a direction passing through the origin in parallel to the base and orthogonal to the X direction is set to a Y direction; ρ is a function of permittivity; ϕ is the reconstruction function; $\phi_R$ is a function satisfying $\phi = \phi_R \delta(x)$; $k_x$, $k_y$, and $k_z$ are respectively x, y and z components of a wave number; k is a time wave number; and θ is a rotation angle with an axis of the cone as a rotation axis.

Consequently, it is possible to image internal information of a target object having an approximately conical shape with higher accuracy and at a high speed.

The shape indicated by the analysis model may be a shape of a substantial cone having a curved generating line, the imaging function may be expressed by the following Equation (C), and the image reconstruction unit may reconstruct the image regarding the internal information of the target object by using a function expressed by the following Equation (D) which is obtained by integrating the imaging function with θ.

[Math. 10]

$$\rho(x, y, z, \theta) = \int_{-\infty}^{\infty} \phi(x, y, z, k) dk \quad (C)$$
$$= \int_{-\infty}^{\infty} \left[ \frac{1}{(2\pi)^2} \int_{-\infty}^{\infty} \int_{-\infty}^{\infty} e^{-i(k_x x + k_y y)} a_\theta(k_x, k_y, k) \right.$$
$$\left. e^{iz\sqrt{4k^2 - k_x^2 - k_y^2}} dk_x dk_y \right] dk$$
$$= \frac{1}{(2\pi)^2} \int_{-\infty}^{\infty} \int_{-\infty}^{\infty} \int_{-\infty}^{\infty} e^{-i(k_x x + k_y y - k_z z)} a_\theta(k_x, k_y, k)$$
$$\left(\frac{dk}{dk_z}\right) dk_x dk_y dk_z$$

$$k_z = \sqrt{4k^2 - k_x^2 - k_y^2}$$

$$\frac{dk}{dk_z} = \frac{d}{dk_z}\left(\frac{1}{2}\sqrt{k_x^2 + k_y^2 + k_z^2}\right) = \frac{1}{2} \frac{k_z}{\sqrt{k_x^2 + k_y^2 + k_z^2}}$$

[Math. 11]

$$P(X, Y, Z) = \int_0^{2\pi} \rho(x, y, z, \theta) d\theta \quad (D)$$

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the substantial cone is set to the origin, a direction directed from the origin toward the center of a base of the substantial cone is set to a Z direction, a direction passing through the origin in parallel to the base is set to an X direction, and a direction passing through the origin in parallel to the base and orthogonal to the X direction is set to a Y direction; ρ is a function of permittivity; ϕ is the reconstruction function; $a_\theta$ is a coefficient; $k_x$, $k_y$, and $k_z$ are respectively x, y and z components of a wave number; k is a time wave number; and θ is a rotation angle with an axis of the substantial cone as a rotation axis.

Consequently, it is possible to image internal information of a target object having a substantially conical shape with higher accuracy and at a high speed.

The shape indicated by the analysis model may be a shape of an asymmetric pyramid, the imaging function may be expressed by the following Equation (F) in a case where each of ξ, η, and ζ is a variable satisfying the following Equation (E), and, the image reconstruction unit may reconstruct the image regarding the internal information of the target object by using a function expressed by the following Equation (G) which is obtained by integrating the imaging function with θ.

[Math. 12]

$$\xi = -k_x\cos\theta + \{k_y\cos\alpha(\theta) + k_z\sin\alpha(\theta)\}\sin\theta$$
$$\eta = -k_x\sin\theta - \{k_y\cos\alpha(\theta) + k_z\sin\alpha(\theta)\}\cos\theta$$
$$\zeta = -k_y\sin\alpha(\theta) + k_z\cos\alpha(\theta)$$
$$k_x = -\xi\cos\theta - \eta\sin\theta$$
$$k_y = (\xi\sin\theta - \eta\cos\theta)\cos\alpha(\theta) - \zeta\sin\alpha(\theta)$$
$$k_z = (\xi\sin\theta - \eta\cos\theta)\sin\alpha(\theta) + \zeta\cos\alpha(\theta)$$

(E)

[Math. 13]

$$\rho(x, y, z, \theta) = \frac{1}{(2\pi)^2}\int_{-\infty}^{\infty}\int_{-\infty}^{\infty}\int_{-\infty}^{\infty}e^{i(\xi X + \eta Y + \zeta Z)}\tilde{\phi}_R(k_y, k, \theta)$$
$$\left(\frac{dk}{dk_z}\right)d\xi d\eta d\zeta$$

(F)

$$k = \frac{1}{2}\sqrt{k_x^2 + k_y^2 + k_z^2} = \frac{1}{2}\sqrt{\xi^2 + \eta^2 + \zeta^2}$$

$$\frac{dk}{dk_z} = \frac{k_z}{2\sqrt{k_x^2 + k_y^2 + k_z^2}} = \frac{(\xi\sin\theta - \eta\cos\theta)\sin\alpha + \zeta\cos\alpha}{2\sqrt{\xi^2 + \eta^2 + \zeta^2}}$$

[Math. 14]

$$P(X, Y, Z) = \int_0^{2\pi}\rho(x, y, z, \theta)d\theta$$

(G)

Here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the pyramid is set to the origin, a direction directed from the origin toward the center of a base of the pyramid is set to a Z direction, a direction passing through the origin in parallel to the base is set to an X direction, and a direction passing through the origin in parallel to the base and orthogonal to the X direction is set to a Y direction; ρ is a function of permittivity; φ is the reconstruction function; $\phi_R$ is a function satisfying $\phi=\phi_R\delta(x)$; $a_\theta$ is a coefficient; $k_x$, $k_y$, and $k_z$ are respectively x, y and z components of a wave number; k is a time wave number; θ is a rotation angle with an axis of the pyramid as a rotation axis; and α is an inclined angle with the Z direction as a reference.

Consequently, it is possible to image internal information of a target object having a substantially asymmetric pyramidal shape with higher accuracy and at a high speed.

The imaging apparatus may further include a probe in which the receiving antenna element and the transmitting antenna element are integrally provided, and an electric wave absorbing portion may be located between the receiving antenna element and the transmitting antenna element.

Consequently, it is possible to reduce the magnitude of a wave which is directly received by the receiving antenna element among waves transmitted from the transmitting antenna element, and thus to increase a ratio of the magnitude of a scattered wave from a target object received by the receiving antenna element to the magnitude of the wave directly received. Therefore, it is possible to obtain a clearer image of the inside of a target object.

The shape indicated by the analysis model may be a shape of a cone, and the transmitting antenna element and the receiving antenna element may be integrally moved along a line corresponding to a generating line of a cone in the target object.

Consequently, in an analysis model in which the sensor element is moved on a generating line of a cone, a partial differential equation for inverse problem is set, and internal information of a target object can be imaged versatilely and at a high speed by solving the equation. Particularly, it is possible to image internal information of a target object having a conical shape with higher accuracy and at a high speed.

The shape indicated by the analysis model may be a shape of a substantial cone having a curved generating line, and the transmitting antenna element and the receiving antenna element may be integrally moved along a line corresponding to a curved generating line of a substantial cone in the target object.

Consequently, in an analysis model in which the sensor element is moved on a generating line of a substantial cone having a curved generating line, a partial differential equation for inverse problem is set, and internal information of a target object can be imaged versatilely and at a high speed by solving the equation. Particularly, it is possible to image internal information of a target object having a substantially conical shape, for example, a hemispherical shape or a dome-like shape with higher accuracy and at a high speed.

The shape indicated by the analysis model may be a shape of an asymmetric pyramid, and the transmitting antenna element and the receiving antenna element may be integrally moved along a line corresponding to a generating line of an asymmetric pyramid in the target object.

Consequently, in an analysis model in which the sensor element is moved on a generating line of an asymmetric pyramidal shape, a partial differential equation for inverse problem is set, and internal information of a target object can be imaged versatilely and at a high speed by solving the equation. Particularly, it is possible to image internal information of a target object having a shape in which a part of a conical shape or a substantially conical shape is omitted, or target objects having various curved shapes with higher accuracy and at a high speed.

The wave may be a microwave.

Consequently, it is possible to image internal information of a target object according to a versatile and simple method regardless of an amount of water of a target object.

The wave may be a pulse wave or a periodic wave with a predetermined frequency.

Consequently, it is possible to image internal information of a target object having various curved shapes according to a versatile and simple method.

Advantageous Effects of Invention

According to the present invention, it is possible to perform analysis of an inverse problem versatilely and at a high speed, and to easily image internal information of objects having various curved shapes. It is possible to image internal information of target objects having various curved shapes with higher accuracy and at a high speed.

BRIEF DESCRIPTION OF THE DRAWINGS

The above-described object, and other objects, features and advantages will become more apparent on the basis of preferred embodiments described below and the following accompanying drawings.

Figure 1:
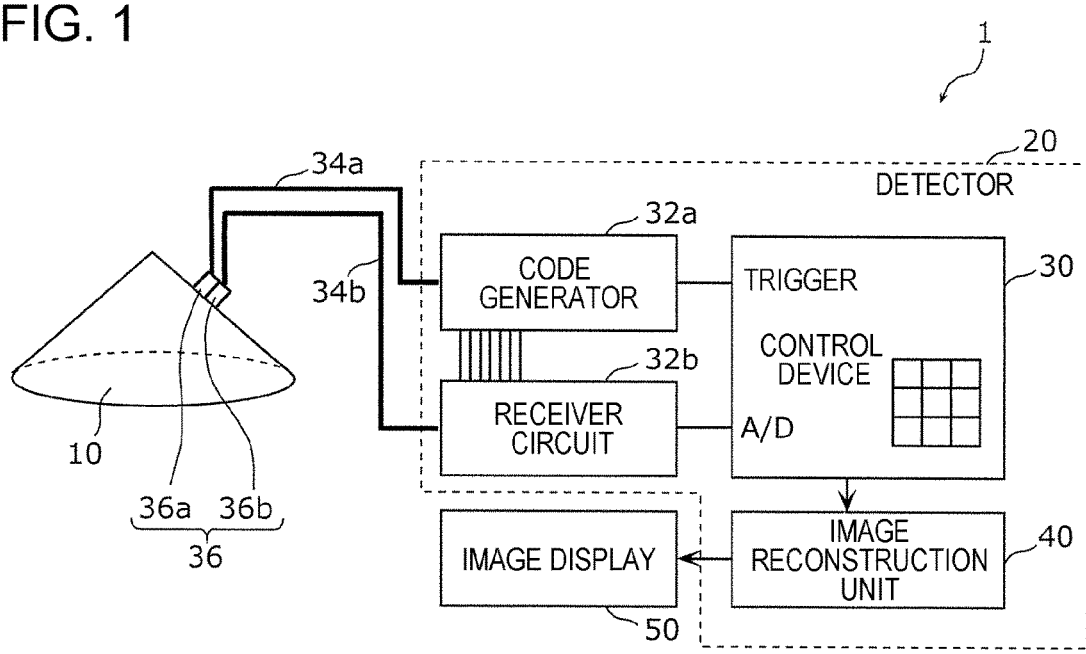
FIG. 1 is a schematic diagram illustrating a configuration of a mammography apparatus according to Embodiment 1.

DESCRIPTION OF EMBODIMENTS (Findings as Basis of Present Invention)

Prior to description of embodiments of the present invention, a description will be made of a technique providing a basis of the present invention.

An examination method and an examination apparatus according to the present invention are examination techniques using scattering tomography.

The scattering tomography is a technique of imaging internal information of an object by observing and analyzing scattered waves of when waves are radiated to the object. In other words, the examination apparatus and the examination method according to the present invention are techniques of detecting a defect or the like of an object in a nondestructive manner by analyzing scattered waves generated by radiating waves to the object. A detailed principle of the scattering tomography is as follows.

Generally, a scattering phenomenon occurring when waves are radiated to an object may be expressed by using operators. For example, a physical equation represented by an object O, a radiation wave u, and observation data p may be expressed as $p=A_u[O]$ by using an operator A. Here, in a case where the object O, the radiation wave u, and the operator (system function) A are known, a problem of obtaining the observation data p is called a forward problem.

In contrast, a major problem in terms of medical care or industry is a problem of obtaining a state of the object O in a case where the radiation wave u, the system function A, and the observation data p are known. This problem is called an inverse problem in the sense that the causal relation of physical phenomena is traced in an inverse direction, and may be expressed as $O=A_u^{-1}[p]$. The scattering tomography uses the inverse problem.

As an example using the scattering tomography, there is a multi-path linear array radar (MPLA radar). In this method, for example, an antenna element as a sensor element is attached to a target object, even the target object with a curvature is approximated to a plane, and a defect or the like of the target object is detected in a nondestructive manner on the basis of a relationship between an electromagnetic wave radiated from the antenna element and a reflected wave (scattered wave) reflected at the target object.

Antenna elements used in the MPLA radar are formed of a plurality of transmitting antenna elements radiating waves to a target object, and a plurality of receiving antenna elements receiving scattered waves generated at the target object. An arrangement position of each antenna element is determined in an analysis model supposed beforehand. A scattered wave of a wave radiated from a transmitting antenna element disposed at a certain position is received by a receiving antenna element disposed at another position. Consequently, in the MPLA radar, multistatic analysis is performed by using scattered waves received by the receiving antenna elements, and internal information of an object is imaged.

Here, internal information of a living body can be imaged by supposing a living body model as an analysis model. For example, if the breast is supposed as analysis model, this can be used as mammography for measuring a position and a size of cancer tissue inside the breast.

In a case where internal information is imaged by using a living body as a target object, a shape of the target object does not always match a supposed analysis model. Particularly, in a case where a target object has a flexible shape, the shape of the target object changes depending on an arrangement position or direction, and thus a problem that a receiving antenna element in the supposed analysis model cannot normally receive a scattered wave occurs. Therefore, a position of the antenna element and the intensity of a received signal may not be accurately specified, and thus accurate internal information may not be recognized in a case where analysis is performed.

In the examination method and the examination apparatus of the present invention, analysis is performed while freely moving antenna elements formed of a pair of a transmitting antenna element and a receiving antenna element on a target object in an analysis model of the target object supposed beforehand. In other words, in the examination method and the examination apparatus of the present invention, of the pair of the transmitting antenna element and the receiving antenna element, a wave is radiated to the target object from the transmitting antenna element, and a scattered wave thereof is received by the receiving antenna element forming the pair with the transmitting antenna radiating the wave. Consequently, in the mammography, monostatic analysis is performed by using the scattered wave received by the receiving antenna element, and thus internal information of the object is imaged.

Hereinafter, with reference to the drawings, embodiments of the present invention will be described. In the following embodiments, as an example, a description will be made of mammography for measuring a position and a size of cancer tissue inside the breast by using the breast as an examination target object. In the drawings, a constituent element with same reference numeral indicates the same or similar constituent element.

An embodiment described below indicates one preferable specific example of the present invention. Numerical values, shapes, materials, constituent elements, arrangement positions of the constituent elements, connection forms, steps, and the order of steps described in the following embodiment are only examples, and are not intended to limit the present invention. Among constituent elements in the following embodiment, constituent elements not cited in an independent claim showing the top concept of the present invention will be described as any constituent elements configuring a more preferable aspect.

Embodiment 1

<Configuration of Examination Apparatus>

Hereinafter, a description will be made of a configuration of the examination apparatus according to Embodiment 1 with reference to FIGS. 1 to 3. In the present embodiment, as an example of imaging internal information of a living body, particularly, position information of defective tissue, a cone having a linear generating line is used as a model. Specifically, as examples, a mammography apparatus will be described as the examination apparatus, the breast will be described as a target object having a substantially conical shape, and cancer tissue in the breast will be described as defective tissue. In this apparatus, a transmitting antenna element and a receiving antenna element forming a probe which is a sensor element are moved along a generating line of a cone. In other words, the transmitting antenna element and the receiving antenna element are integrally moved along a line corresponding to a generating line of a cone in a target object. Here, the line corresponding to the generating line of the cone is a line corresponding to a generating line of a cone in a case where a shape of a target object 10 is regarded as a conical shape.

FIG. 1 is a schematic diagram illustrating a configuration of a mammography apparatus according to the present embodiment. FIG. 2 is a schematic diagram illustrating a configuration of a probe in the mammography apparatus according to the present embodiment. FIG. 3 is a diagram illustrating an example of a method for using the probe illustrated in FIG. 2.

First, a description will be made of a configuration of a mammography apparatus 1 according to the present embodiment.

As illustrated in FIG. 1, the mammography apparatus 1 includes a probe 36 and a detector 20.

Figure 2:
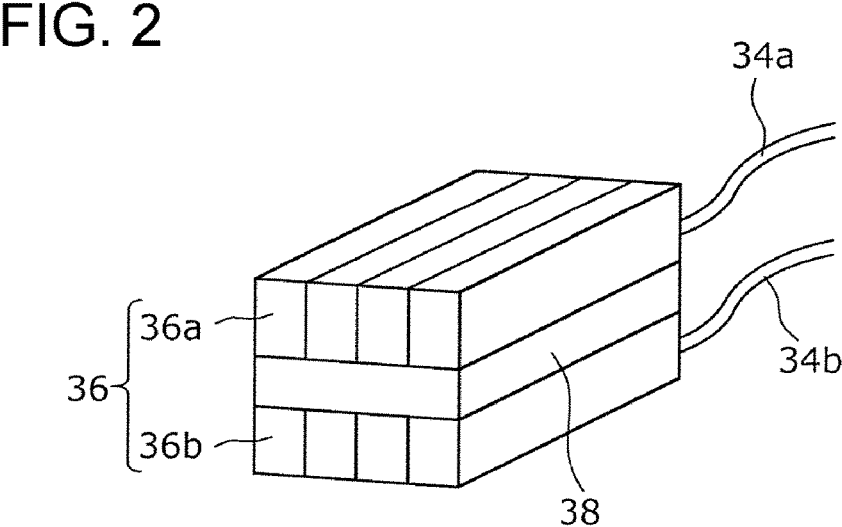
FIG. 2 is a schematic diagram illustrating a configuration of a probe in the mammography apparatus according to Embodiment 1.

The probe 36 is a sensor element measuring internal information of the target object 10, and is formed of a pair of a transmitting antenna element 36a and a receiving antenna element 36b as illustrated in FIG. 2. The transmitting antenna element 36a and the receiving antenna element 36b may be respective antenna arrays having a plurality of transmitting points and receiving points.

As illustrated in FIG. 2, the probe 36 has a configuration in which the transmitting antenna element 36a and the receiving antenna element 36b are joined together through a wave absorbing portion (electric wave absorbing portion) 38. The transmitting antenna element 36a and the receiving antenna element 36b are respectively connected to coaxial cables 34a and 34b. The wave absorbing portion is a portion absorbing a wave received by the transmitting antenna element 36a, and is an electric wave absorbing portion in a case where a wave is an electric wave such as a microwave. Here, a description will be made of an example in which the wave absorbing portion is an electric wave absorbing portion, but the present invention is not limited to this example.

Relative positions between the transmitting antenna element 36a and the receiving antenna element 36b are fixed in the probe 36. However, a configuration of the probe 36 is not limited to this configuration. Preferably, the transmitting antenna element 36a and the receiving antenna element 36b are integrally provided through the electric wave absorbing portion 38. In other words, preferably, in the probe 36, the receiving antenna element 36b and the transmitting antenna element 36a are integrally provided, and the electric wave absorbing portion 38 is located between the receiving antenna element 36b and the transmitting antenna element 36a.

The phrase "integrally provided" indicates a state in which the transmitting antenna element 36a and the receiving antenna element 36b are provided in the probe 36, and the transmitting antenna element 36a and the receiving antenna element 36b are moved together. A case where the transmitting antenna element 36a and the receiving antenna element 36b are integrally provided includes not only a case where the transmitting antenna element 36a and the receiving antenna element 36b are disposed to be close to each other through the electric wave absorbing portion 38 but also a case where there are gaps between the antenna elements and the electric wave absorbing portion 38. The case where there are gaps between the antenna elements and the electric wave absorbing portion 38 is a case where the electric wave absorbing portion is disposed in a state in which there is a gap at least one of between the transmitting antenna element 36a and the electric wave absorbing portion 38 and between the receiving antenna element 36b and the electric wave absorbing portion 38. The electric wave absorbing portion 38 may employ an electric wave absorber (wave absorber) disposed between the transmitting antenna element 36a and the receiving antenna element 36b.

The phrase "through the electric wave absorbing portion 38" also includes a case where an electric wave absorbing material (wave absorbing material) is attached to one surface of the transmitting antenna element 36a directed toward the receiving antenna element 36b or one surface of the receiving antenna element 36b directed toward the transmitting antenna element 36a in a film form according to a method such as coating, or a case where a tabular component made of the electric wave absorbing material is adhered and fixed onto the surface. The electric wave absorbing portion 38 may reduce the magnitude of a microwave (wave) which is directly received by the receiving antenna element 36b among microwaves (waves) transmitted from the transmitting antenna element 36a. The electric wave absorbing material is a conductive material, and is, specifically, metal, carbon, or the like. With this configuration, it is possible to reduce the magnitude of a microwave (wave) which is directly received by the receiving antenna element 36b among microwaves (waves) transmitted from the transmitting antenna element 36a, and thus to increase a ratio of the magnitude of a reflected wave (scattered wave) from the target object 10 received by the receiving antenna element 36b to the magnitude of the microwave (wave) directly received. In other words, it is possible to obtain a clearer image of the inside of a target object by providing the electric wave absorbing portion 38.

A code generated by a code generator 32a propagates to the transmitting antenna element 36a through the coaxial cable 34a.

A signal received by the antenna element 36b propagates to a receiver circuit 32b through the coaxial cable 34b. Consequently, the receiver circuit 32b detects the received signal.

Figure 3:
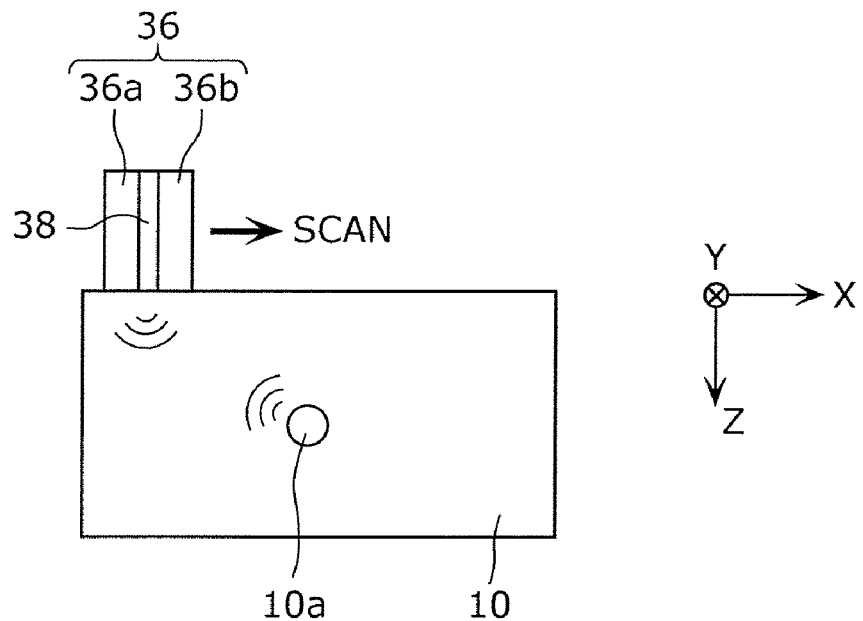
FIG. 3 is a diagram illustrating an example of a method for using the probe illustrated in FIG. 2.

As illustrated in FIG. 3, the probe 36 measures internal information of the target object 10 while being moved on the target object 10 in response to an instruction (operation) from a user. The probe 36 is configured to be freely moved with respect to the target object 10. The transmitting antenna element 36a transmits a wave toward the target object 10, and the receiving antenna element 36b receives a scattered wave which is scattered at a scatterer 10a inside the target object 10. Herein, a microwave is described as an example of a wave, but a wave is not limited to a microwave, and an electric wave or an ultrasonic wave with other bandwidths may be used.

As illustrated in FIG. 1, the detector 20 includes a control device 30, an image reconstruction unit 40, the code generator 32a, and the receiver circuit 32b.

The control device 30 controls transmission of a wave to the target object 10 from the code generator 32a, reception of a scattered wave in the receiver circuit 32b, and analysis of a received scattered wave in the image reconstruction unit 40. The control device 30 causes a trigger signal to propagate to the code generator 32a.

Under the control of the control device 30, the mammography apparatus 1 transmits a wave to the target object from the transmitting antenna element 36a, receives a scattered wave from the scatterer 10a with the receiving antenna element 36b, and analyzes the scattered wave with the image reconstruction unit 40 so as to generate an image.

The code generator 32a generates a wave radiated from the transmitting antenna element 34a as a code on the basis of a trigger signal from the control device 30, and carries the code to the transmitting antenna element 34a. The code generator 32a generates, as a code, for example, a transmission timing of a wave radiated from the transmitting antenna element 36a, the number of times thereof, and a transmission gain. A wave radiated to the target object 10 from the transmitting antenna element 36a is, for example, a microwave.

The receiver circuit 32b carries data regarding a scattered wave of the microwave received by the receiving antenna element 36b, to the image reconstruction unit 40. In this case, the data regarding the received scattered wave may be amplified by the receiver circuit 32b or may undergo signal processing such as AD conversion in the control device 30.

The image reconstruction unit 40 analyzes the data regarding the scattered wave carried from the receiver circuit 32b, and images the data regarding the scattered wave according to an image reconstruction algorithm which will be described later. Consequently, a video corresponding to internal information of the target object 10 is reproduced on an image display 50.

The image display 50 is a monitor screen, and outputs data calculated by the image reconstruction unit 40 as a video.

As an analysis model used for the image reconstruction algorithm, an analysis model having a conical shape or a substantially conical shape may be supposed. For example, in the present embodiment, as an example, a conical analysis model of which a diameter of the circle of the base is 30 cm is supposed. In the analysis model, the probe 36 may be moved linearly along a generating line directed toward the base from the vertex of the cone. In other words, the transmitting antenna element 36a and the receiving antenna element 36b may be moved linearly in the same direction as an axis of rotation symmetry of the cone when seen in a plan view from at least one direction. Here, the axis of rotation symmetry of the cone indicates a straight line connecting the vertex of the cone to the center of the base of the cone. The image reconstruction algorithm will be described later in detail.

The transmitting antenna element 36a and the receiving antenna element 36b are moved in a pair.

Hereinafter, a description will be made of procedures of observation (imaging) of internal information of a living body, that is, position information of cancer tissue in the breast in the mammography apparatus 1 according to the present embodiment.

<Observation Procedures for Internal Information of Living Body>

Figure 4:
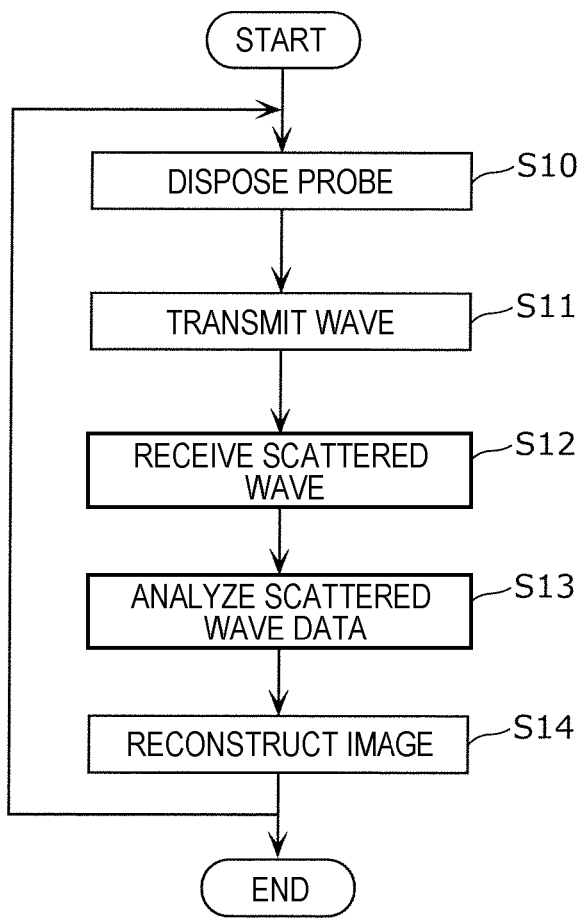
FIG. 4 is a flowchart illustrating an operation of the mammography apparatus according to Embodiment 1.

FIG. 4 is a flowchart illustrating an operation of the mammography apparatus 1 according to the present embodiment illustrated in FIG. 1.

As illustrated in FIG. 4, the a method of imaging internal information of internal information of the breast which is the target object 10 in the mammography apparatus 1 is as follows.

First, the probe 36 is disposed on the target object 10 (S10) A wave is radiated toward the target object 10 from the transmitting antenna element 36a (S11). For example, a microwave is used as the wave. A wavelength, amplitude, and the like of the microwave are adjusted in the code generator 32a, and the microwave is radiated to the target object 10 from the transmitting antenna element 36a.

Next, scattered waves (scattered waves) reflected at normal tissue and cancer tissue of the inside of the target object 10 are received by the receiving antenna element 36b (S12). The normal tissue and the cancer tissue correspond to the scatterer 10a illustrated in FIG. 3. In a case where a wave is an electromagnetic wave such as a microwave, permittivity differs between the normal tissue and the cancer tissue, and thus intensities of scattered waves are different from each other. The received scattered wave may be amplified in the receiver circuit 32b, or may be converted to have a format appropriate for analysis in the image reconstruction unit 40 through, for example, AD conversion.

Next, scattered wave data indicating the received scattered wave is carried from the receiver circuit 32b to the image reconstruction unit 40. The image reconstruction unit 40 analyzes the carried scattered wave data (S13). Herein, the scattered wave data is analyzed according to the image reconstruction algorithm described below. Specifically, an imaging function is derived. Consequently, videos (images) corresponding to the normal tissue and the cancer tissue of the inside of the target object 10 are reconstructed (S14). The probe 36 is moved to be disposed at another observation position on the target object 10 (S10), and the above-described procedures are repeatedly performed. Data obtained through reconstruction using the imaging function is not required to be a moving image, and may be an image, that is, a still image.

Data regarding a reconstructed video is carried from the image reconstruction unit 40 to the monitor 50, and is displayed on the monitor 50. Consequently, it is possible to recognize the presence, a position, a shape, and a size of the cancer tissue of the inside of the target object 10.

As described above, the image reconstruction unit 40 reconstructs an image regarding internal information of the target object 10 on the basis of the scattered wave data indicating the scattered wave received by the receiving antenna element 36b. Specifically, the image reconstruction unit 40 derives a reconstruction function by solving a partial differential equation by using the scattered wave data and an analysis model indicating a shape. An image regarding internal information of the target object 10 is reconstructed by using the reconstruction function. Here, the partial differential equation is an equation satisfied by the reconstruction function for reconstructing an image regarding internal information of the target object.

Specifically, the partial differential equation is an equation expressed by using independent variables indicating positions of transmitting points and receiving points inside the target object. The partial differential equation is a linear partial differential equation having, as a solution, a scattering field function which is a function of a field where a scattered wave is generated at each point in a space having the same order as the number of independent variables. The image reconstruction unit derives an imaging function which is a limiting value of a time variable of the reconstruction function, and reconstructs an image regarding internal information of the target object by using the imaging function.

Hereinafter, the image reconstruction algorithm executed by the image reconstruction unit 40 will be described. The image reconstruction algorithm corresponds to an image reconstruction principle of the mammography apparatus 1 which uses a pyramid having a linear generating line as an analysis model according to the present embodiment.

<Image Reconstruction Algorithm>

Figure 5:
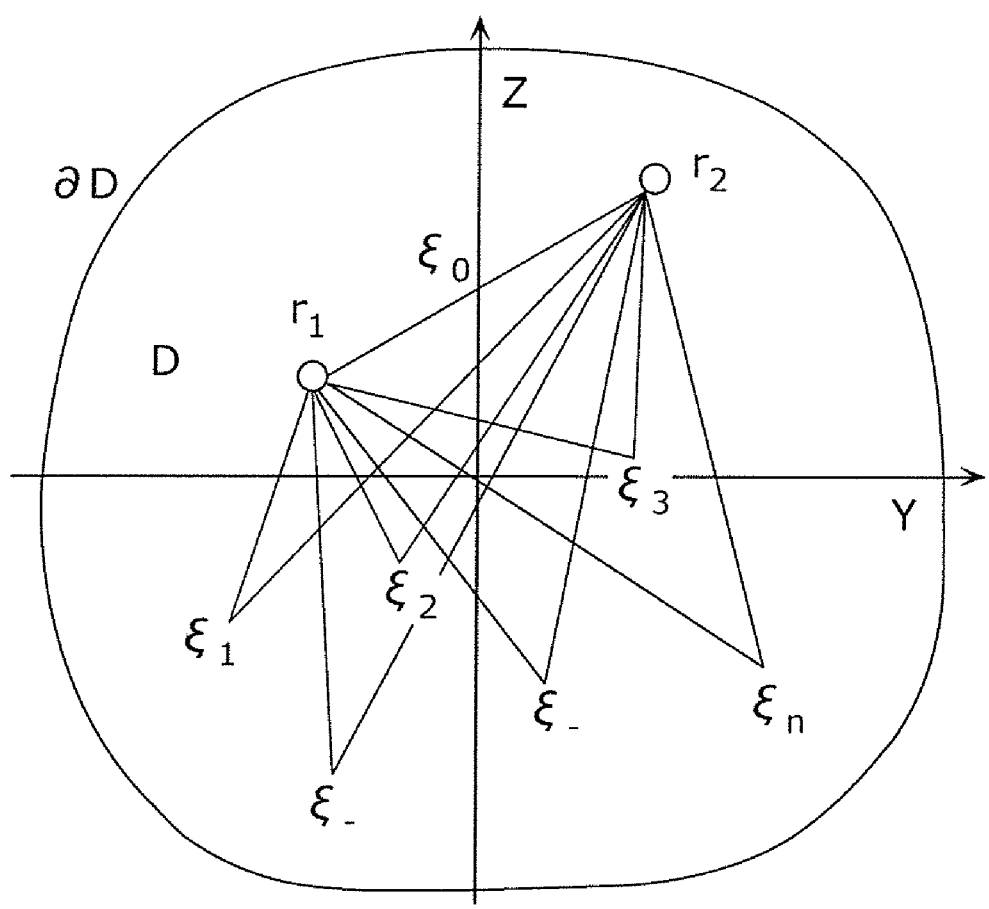
FIG. 5 illustrates an analysis model for explaining a principle of a mammography method according to Embodiment 1.
Figure 6:
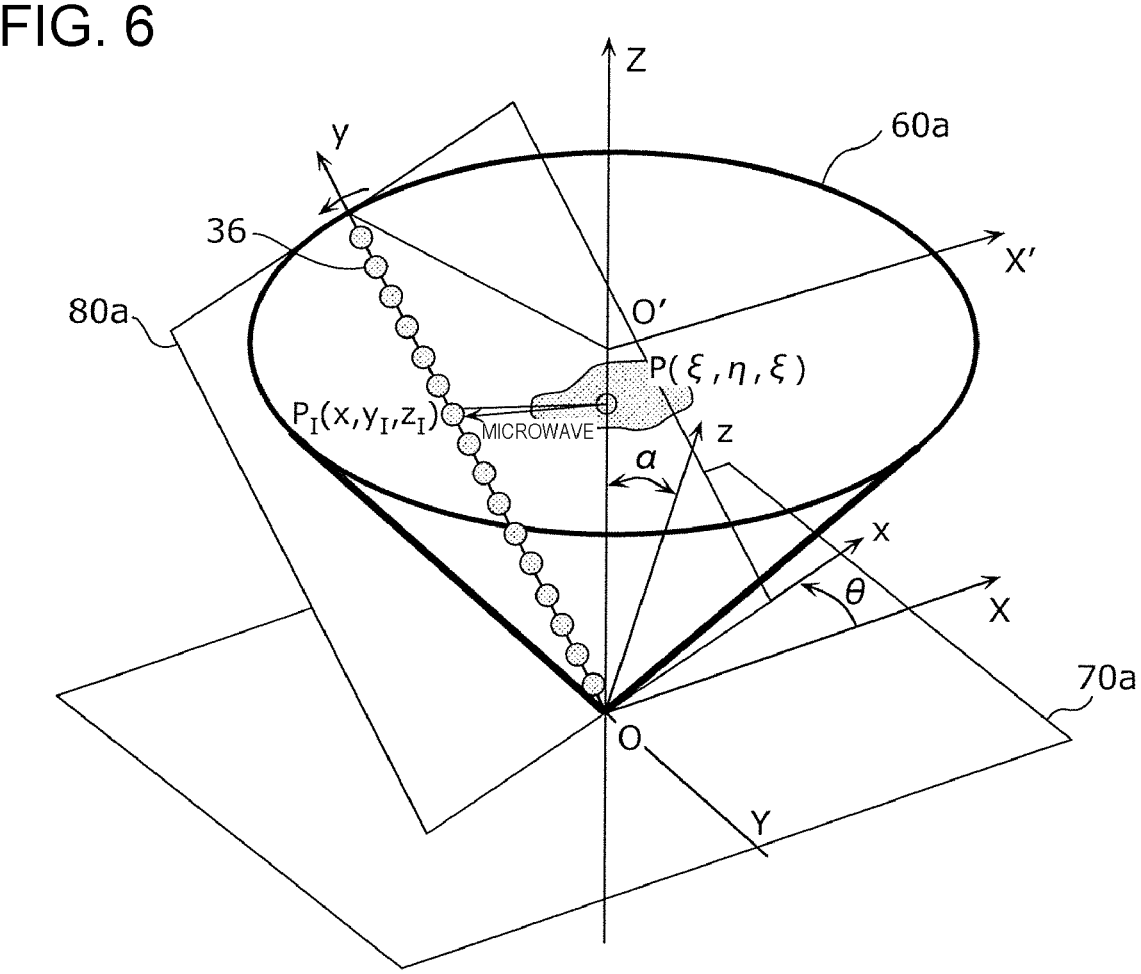
FIG. 6 illustrates an analysis model for explaining a principle of the mammography method according to Embodiment 1.
Figure 7:
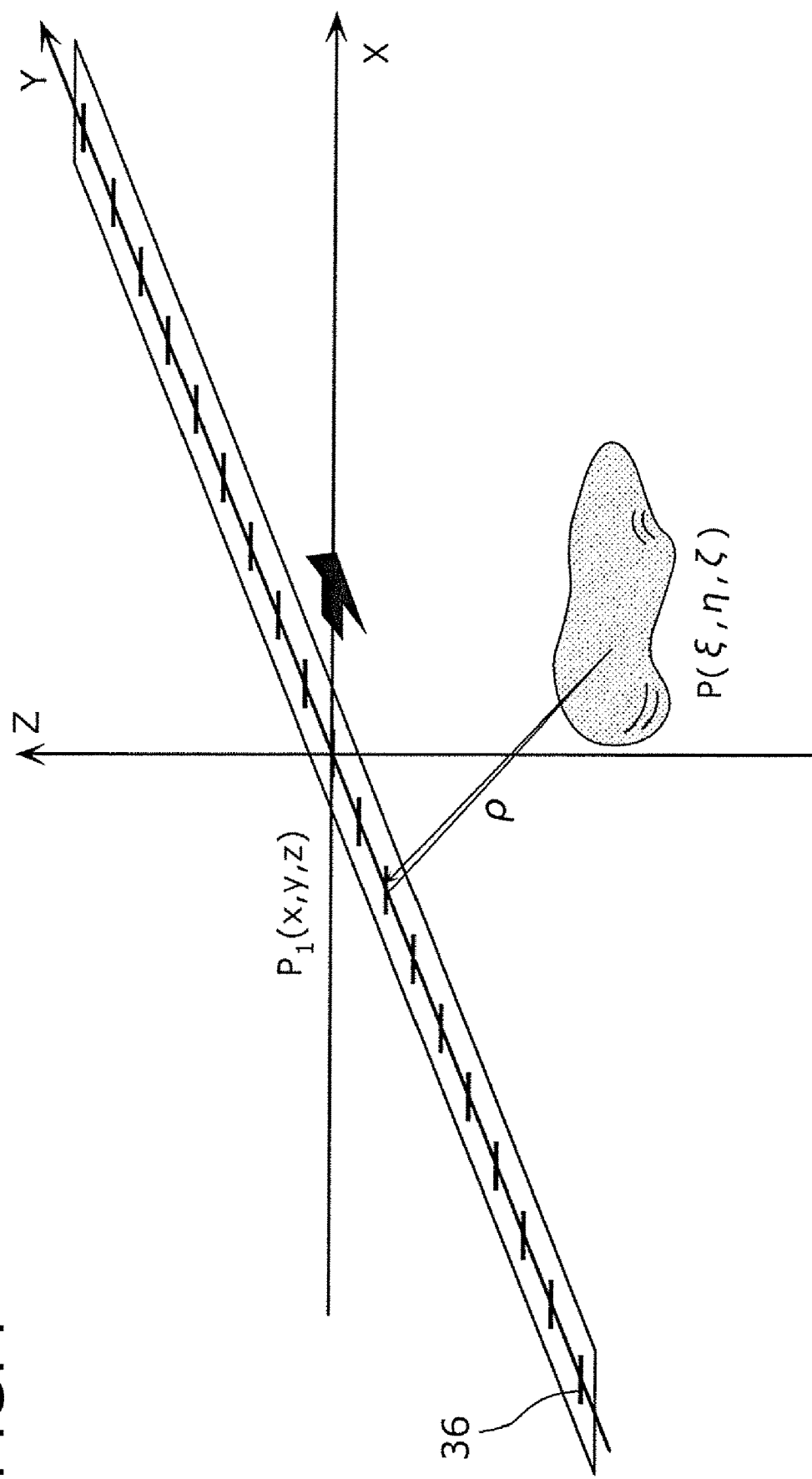
FIG. 7 illustrates an analysis model for explaining a principle of the mammography method according to Embodiment 1.

FIGS. 5 to 7 illustrate analysis models for explaining a principle of a scattering tomography method according to the present embodiment.

In the image reconstruction algorithm (theory) described below, it is assumed that an imaging target is a cone having a linear generating line. By using the cone as an analysis model, a radiation point (transmitting antenna element 36a) and a receiving point (receiving antenna element 36b) of a wave are provided at any positions on the generating line. In other words, an analysis model is formed such that the probe 36 is moved on the generating line of the cone. In this image reconstruction algorithm, monostatic analysis in which the radiation point and the receiving point are assumed to be located at the same position is performed. Internal information of an imaging target is imaged by using transmission data indicating a radiated wave which is radiated from the radiation point and scattered wave data indicating a scattered wave received at the receiving point.

When the image reconstruction algorithm is described briefly in terms of mathematics, in the algorithm, an inverse problem is solved; that is, a solution (function) which is necessary for imaging is first set, an equation is built on the basis of the solution, and a more accurate solution is obtained by using transmission data and reception data.

In other words, first, a Green's function (reconstruction function) which is necessary for imaging is set. A partial differential equation regarding a three-dimensional space formed of four variables such as (t,x,y,z) of which the function is a solution (function) is built. The partial differential equation is solved by using transmission data radiated from the transmitting antenna element 36a and reception data (scattering data) received by the receiving antenna element 36b as boundary conditions. Consequently, the imaging function is obtained, and internal information of an object can be imaged with high quality and at a high speed.

Detailed description is as follows.

1. Inverse Problem of Scattering and Green's Function

In FIG. 5, a situation is considered in which a wave emitted from a point $r_1$ is reflected at a point so as to be returned to a point $r_2$. Here, in the mammography apparatus 1 according to the present embodiment, the point $r_1$ and the point $r_2$ are located at the same position. Under the condition that a frequency ω is constant, the transmitting point $r_1$ and the receiving point $r_2$ of a wave are freely moved inside an x section D (a side surface of a cone 60a). If data obtained in this case is indicated by $G(r_1, r_2, \omega)$, this function relates to a distribution of reflection points in a region. Here, w is an angular frequency, and ω=2πf. $G(r_1, r_2, \omega)$ is a sum of reflected signals from all points ξ, and, since there are many reflection points in the region, and $G(r_1,r_2,\omega)$ may be written as in the following Equation (1).

[Math. 15]

$$G(r_1, r_2, \omega) = \iiint_D \varphi(r_1 \to \xi \to r_2, \omega) d\xi \tag{1}$$

Here,

[Math. 16]

$$\varphi(r_1 \to \xi \to r_2, \omega)$$

indicates a signal intensity of a wave which is emitted from the point $r_1$, and is reflected at the point ξ so as to be returned to the point $r_2$. The parameters $r_1$ and $r_2$ in the expression are vectors, and are boldface in the expression.

Here, coordinates of the transmitting point $r_1$ and the receiving point $r_2$ of a wave are the same as each other at all times.

A description will be made of a theoretical structure of an inverse problem of scattering by using the function $G(r,\omega) \equiv G(r_1,r_2,\omega)$.

A partial region of a three-dimensional space is indicated by D, and a boundary thereof is indicated by ∂D. In this case, the function $G(r,\omega)$ is a solution of a differential equation as shown in the following Equation (2) in the region D.

[Math. 17]

$$L\left(\frac{\partial}{\partial t}, \frac{\partial}{\partial r}\right)\overline{G}(r, t) = 0 \tag{2}$$

Here, $\overline{G}(r,t)$ is a function obtained by performing Fourier transform on $G(r,\omega)$ with respect to ω.

Values of the $G(r,\omega)$ at the boundary ∂D are assumed to be measured values (transmission data and reception data) in the probe 36. The equation is solved under the boundary condition, and a function ρ(r) regarding a gradient of permittivity in the region D to be obtained is defined on the basis of the result. Actually, differential operators $L(\partial/\partial t, \partial/\partial r_1, \partial/\partial r_2)$ appearing here are required to be obtained.

2. Multi-Path Reverse Scattering Theory on Rotationally Symmetric Curved Surface, Using Cone as Analysis Model Next, a description will be made of a method of obtaining the above-described differential operators. FIGS. 6 and 7 illustrate analysis models for explaining a method of obtaining the differential operators.

In an analysis model according to the present embodiment, as illustrated in FIG. 6, an imaging target is assumed to be the cone 60a having a linear generating line. The probe 36 is moved linearly along the generating line of the cone 60a. The probe 36 may be rotationally moved centering on an axis passing through the vertex of the cone 60a and the center of the base of the cone 60a. In other words, measurement is performed while the transmitting antenna element 36a and the receiving antenna element 36b are being moved linearly in the same direction as an axis of rotational symmetry of the cone 60a used as the analysis model when seen in a plan view from at least one direction. Here, the axis of rotational symmetry of the cone indicates a straight line connecting the vertex of the cone to the center of the base of the cone.

Specifically, it is assumed that a tangential plane 80a of the cone 60a at a position of the probe 36 is supposed, the virtual tangential plane 80a is rotated, and scattered wave data is obtained with respect to all rotation angles 6. A three-dimensional internal structure of the cone 60a is reconstructed on the basis of monostatic time series data in the surface of the cone 60a. A theory thereof will now be described.

In this analysis model, as illustrated in FIG. 6, the vertex of the cone 60a is indicated by a point O, and the center of the circle of the base of the cone 60a is indicated by a point O'. A direction directed from the point O to the point O' is set to a Z direction (Z axis direction). A plane which passes through the point O and is parallel to the base of the cone 60a is set to a reference plane 70a. Any one direction in the reference plane 70a is set to an X direction (X axis direction), and a direction perpendicular to the X direction in the reference plane 70a is set to a Y direction (Y axis direction).

In the base of the cone 60a, a direction which is parallel to the X direction is set to an X' direction (X' axis direction), and a direction which is parallel to the Y axis direction is set to a Y' direction (Y' axis direction).

On the side surface of the cone 60a, a plane which is in contact with the cone 60a at a position of the probe 36 is set to the tangential plane 80a. One direction of an intersection line at which the tangential plane 80a intersects the reference plane 70a is set to an x direction (x axis direction). In the tangential plane 80a, a direction directed from the point O toward the base of the cone 60a is set to a y direction (y axis direction). A direction perpendicular to the x direction and the y direction is set to a z direction (z axis direction).

In the reference plane 70a, it is assumed that the x axis is rotated centering on the Z axis, and an angle formed between the X axis and the x axis is indicated by θ. An angle formed between the Z axis and the z axis is indicated by α.

FIG. 7 is a partially enlarged schematic diagram of a locus of the probe 36 moved on the generating line of the cone 60a illustrated in FIG. 6.

In FIG. 7, if monostatic coordinates $y_1$ and $y_2$ ($y_1=y_2=y$) are defined on the y axis, the following reconstruction theory is established. In the following theory, data regarding a single point ($x=0, y_1, y_2$) is obtained with respect to an x coordinate on the tangential plane 80a.

As illustrated in FIG. 7, a wave radiated from the transmitting antenna 36a at a point $P_1(x, y_1, z)=(x, y, z)$ of the probe 36 is reflected at a point P and received by the receiving antenna 36b at a point $P_2(x, y_2, z)=P_1(x, y, z)$ of the linear array antenna 36. The measurement points $P_1$ and $P_2$ are assumed to be moved on any straight line where the linear array antenna 36 is disposed.

On any straight line, x, y, and z coordinates of $r_1$ and $r_2$ are expressed as $r_1=(x, y_1, z)$ and $r_2=(x, y_2, z)$. In this case, the function G is defined as in the following Equation (3).

[Math. 18]

$$G(r_1, r_2, \omega) = \iiint_D \varphi(r_1 \to \xi \to r_2, \omega) d\xi \quad (3)$$

Next, as an equation satisfied by the function $G(r,\omega)=G(r_1,r_2,\omega)$, a function φ as in the following Equation (4) is introduced. In other words, when the point $P_1$ is moved through the entire region, a signal received at point $P_1$ may be expressed as in the following Equation (4). Here, c is a propagation velocity, and k is a wave number, and, if a wavelength is indicated by λ, relationships of ω=ck, and k=2π/λ are obtained. In addition, φ in Equation (4) corresponds to a reconstruction function (solution) for reconstructing an image regarding internal information of an object in the present invention. Further, ξ, η, and ζ are respectively an x coordinate, a y coordinate, and a z coordinate of the point P(ξ,η,ζ) illustrated in FIGS. 6 and 7. The point P(ξ,η,ζ) is any scattering point in the region. With respect to the vector $r_1$ and the vector $r_2$, a relationship of $r_1=r_2=r(x,y,z)$ is established.

[Math. 19]

$$\varphi(x, y, z) = \int \int_D \int \frac{e^{ik\rho}}{\rho} \frac{e^{ik\rho}}{\rho} \varepsilon(\xi, \eta, \zeta) d\xi d\eta d\zeta \quad (4)$$

$$\rho = \sqrt{(x-\xi)^2 + (y-\eta)^2 + (z-\zeta)^2}$$

Here, a time factor is assumed to be proportional to exp(−iωt) The Kernel function in the integrand term of the above equation is replaced with Φ.

[Math. 20]

$$\phi = \frac{e^{ik\rho}}{\rho} \frac{e^{ik\rho}}{\rho}$$

A partial differential equation having this equation and results of differentiation and integration of the equation with respect to ξ, η, and ζ as solutions is obtained. To do so, high order terms related to 1/ρ generated as a result of differentiation may be disregarded, and calculation may be performed.

Here, shortcuts in differentiation are defined as in the following Expression (5).

[Math. 21]

$$\frac{\partial}{\partial t} \to \partial_t, \frac{\partial}{\partial x} \to \partial_x, \frac{\partial}{\partial y} \to \partial_y, \frac{\partial}{\partial z} \to \partial_z \quad (5)$$

If differentiation of T in each order is obtained by using Expression (5), the following Equation (6) is obtained.

[Math. 22]

$$\partial_x \phi = 2ik \frac{x-\xi}{\rho} \phi + o(\rho^{-3}) \quad (6)$$

$$\partial_y \phi = 2ik \frac{y-\eta}{\rho} \phi + o(\rho^{-3})$$

$$\partial_z \phi = 2ik \frac{z-\zeta}{\rho} \phi + o(\rho^{-3})$$

$$\partial_x \partial_x \phi = (2ik)^2 \frac{(x-\xi)^2}{\rho^2} \phi + o(\rho^{-3})$$

$$\partial_y \partial_y \phi = (2ik)^2 \frac{(y-\eta)^2}{\rho^2} \phi + o(\rho^{-3})$$

$$\partial_z \partial_z \phi = (2ik)^2 \frac{(z-\zeta)^2}{\rho^2} \phi + o(\rho^{-3})$$

In the following equations, the cumbersome term of o(*) is omitted. Here, * indicates any variable. If a sum of four equations regarding second-order differentiation is taken, the following Equation (7) is obtained.

[Math. 23]

$$\Delta_3 \phi = (\partial_x^2 + \partial_y^2 + \partial_z^2)\phi = (2ik)^2 \phi + o(\rho^{-3}) \quad (7)$$

If Equation (7) is summarized, this leads to Equation (8).

[Math. 24]

$$\{\Delta_3 - (2ik)^2 \phi\} = 0 + o(\rho^{-3}) \quad (8)$$

The above Equation (8) is derived assuming a steady state, but is easily expanded to a case of a non-steady state. In order to expand Equation (8) to the case of a non-steady state, replacement of a variable as in the following Expression (9) is performed on Equation (8).

[Math. 25]

$$-ik \to \frac{1}{c}\partial_t \quad (9)$$

In the above-described way, an equation expressed in the following Equation (10) is finally obtained. Equation (10) corresponds to a partial differential equation in the present invention.

[Math. 26]

$$\Delta_3 - \frac{1}{(c/2)^2}\frac{\partial^2}{\partial t^2}\phi = 0 \quad (10)$$

The differentiation in Equation (10) is applied to the integral kernel, and thus φ also satisfies the partial differential equation. The equation is a three-dimensional pseudo wave equation formed of four variables including t, x, y, and z.

Equation (10) is solved by using Fourier transform. First, if multiple Fourier transform is performed on φ with respect to t, x, and y, the following Equation (11) is obtained.

[Math. 27]

$$\tilde{\varphi}(k_x, k_y, z, k) = \int_{-\infty}^{\infty} e^{i\omega t} dt \int_{-\infty}^{\infty} e^{ik_y y} dy \int_{-\infty}^{\infty} e^{ik_z z} \varphi(x, y, z, t) dx \quad (11)$$

If differentiation with respect to z is written as $D_z$ in Equation (11), the following Equation (12) is obtained.

[Math. 28]

$$(D_z^2 - k_x^2 - k_y^2 + 4k^2)\tilde{\varphi} = 0 \quad (12)$$

Here, if the relationship of ω=ck is used, two elementary solutions of Equation (12) are as follows.

[Math. 29]

$$E_1 = e^{iz\sqrt{4k^2 - k_x^2 - k_y^2}} \quad (13)$$

-continued $$E_2 = e^{-iz\sqrt{4k^2 - k_x^2 - k_y^2}}$$

In Equation (13), taking into consideration that a time factor is $e^{-i\omega t}$, a phase is added in the path of a radiated electric wave, and an electric wave reflected from an object rebounds toward a measurement surface, $E_1$ is only a meaningful solution. Therefore, the following Equation (14) is obtained.

[Math. 30]

$$\tilde{\varphi}(k_x, k_y, z, k) = a(k_x, k_y, k) e^{iz\sqrt{4k^2 - k_x^2 - k_y^2}} \quad (14)$$

Fourier transform is performed on this equation, and thus the solution φ of the wave equation (10) is obtained as in the following Equation (15)

[Math. 31]

$$\tilde{\varphi}(x, y, z, k) = \frac{1}{(2\pi)^2} \int_{-\infty}^{\infty} \int_{-\infty}^{\infty} e^{-ik_x x - ik_y y} a(k_x, k_y, k) e^{iz\sqrt{4k^2 - k_x^2 - k_y^2}} dk_x dk_y \quad (15)$$

Measured data is only for x=0, and thus the following Equation (16) is established.

[Math. 32]

$$\phi(x, y, 0, k) = \phi_R(y, k)\delta(x) \quad (16)$$

If this equation is applied to the above equation in which z is assigned with 0, the following Equation (17) is obtained.

[Math. 33]

$$\phi_R(y, k)\delta(x) = \frac{1}{(2\pi)^3}\int_{-\infty}^{\infty}\int_{-\infty}^{\infty}\int_{-\infty}^{\infty} e^{-i(k_x x + k_y y)} a(k_x, k_y, k) dk_x dk_y \quad (17)$$

If Fourier transform is performed on both sides of Equation (17) with respect to (x,y), a $(k_x, k_y, k_z)$ is obtained as follows.

[Math. 34]

$$a(k_x, k_y, k) = \tilde{\phi}_R(k_y, k) \quad (18)$$

In the above-described way, the solution φ(x,y,z,k) of the partial differential equation is obtained.

[Math. 35]

$$\phi(x, y, z, k) = \frac{1}{(2\pi)^2}\int_{-\infty}^{\infty}\int_{-\infty}^{\infty} e^{-i(k_x x + k_y y)} e^{ik_z z} \tilde{\phi}_R(k_y, k) dk_x dk_y \quad (19)$$

In order to perform integration with respect to k, variable transformation is performed according to the following Equation (20)

[Math. 36]

$$k_z = \sqrt{4k^2 - k_x^2 - k_y^2} \quad (20)$$

$$k = \frac{1}{2}\sqrt{k_x^2 + k_y^2 + k_z^2}$$

$$\frac{dk}{dk_z} = \frac{k_z}{2\sqrt{k_x^2 + k_y^2 + k_z^2}}$$

Next, if Fourier transform is performed on Equation (20) with respect to k, and t=0 is applied, as shown in Equation (21), an imaging function ρ(r,θ) in a local coordinate system at the angle θ is obtained.
Here, since

[Math. 37]

$$\overline{\phi}_R(k_{y_1}, k_{y_2}, k)$$

depends on θ, in order to clarify the dependency on θ, the following expression is used.

[Math. 38]

$$\tilde{\phi}_R(k_{y_1}, k_{y_2}, k, \theta)$$

[Math. 39]

$$\rho(x, y, z, \theta) = \int_{-\infty}^{\infty} \phi(x, y, z, k) dk \quad (21)$$

$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)$$

$$\left(\frac{dk}{dk_z}\right) dk_x dk_y dk_z$$

A result obtained at each angle θ is integrated, and thus a three-dimensional reconstructed image shown in Equation (22) is obtained.

[Math. 40]

$$P(X, Y, Z) = \int_0^{2\pi} \rho(x, y, z, \theta) d\theta \quad (22)$$

Next, a result calculated regarding a tangential space is converted into the whole coordinate (X,Y,Z). If projection of the y axis onto an (X,Y) plane is indicated by y', the following Equation (23) is established.

[Math. 41]

$$y = y' \cos \alpha + Z \sin \alpha$$

$$z = -y' \sin \alpha + Z \cos \alpha \quad (23)$$

An equation for transforming (x,y') into (X,Y) is as in the following Equation (24).

[Math. 42]

$$x = X \cos \theta + Y \sin \theta$$

$$y' = -X \sin \theta + Y \cos \theta \quad (24)$$

If the above content is summarized, x, y, and z are obtained as in the following Equation (25).

[Math. 43]

$$x = X \cos \theta + Y \sin \theta$$

$$y = -X \cos \alpha \sin \theta + Y \cos \alpha \cos \theta + Z \sin \alpha$$

$$z = X \sin \alpha \sin \theta - Y \sin \alpha \cos \theta + Z \cos \alpha \quad (25)$$

This transform formula is applied to the following Equation (26).

[Math. 44]

$$\rho(x, y, z, \theta) = \int_{-\infty}^{\infty} \phi(x, y, z, k) dk \quad (26)$$

$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)$$

$$\left(\frac{dk}{dk_z}\right) dk_x dk_y dk_z$$

In a spectral region, variable transformation is performed according to the following Equation (27).
The variables ξ, η, and ζ used in the following Equations (27) and (28) are not the coordinate (ξ,η,ζ) of the point P used in FIG. 7, Equation (22) and the like, and are new variables for variable transformation.

[Math. 45]

$$\xi = -k_x \cos \theta + (k_y \cos \alpha + k_z \sin \alpha) \sin \theta$$

$$\eta = -k_y \sin \theta - (k_y \cos \alpha + k \sin \alpha) \cos \theta$$

$$\zeta = -k_y \sin \alpha + k_z \cos \alpha \quad (27)$$

Inverse transform is according to the following Equation (28)

[Math. 46]

$$k_x = -\xi \cos \theta - \eta \sin \theta$$

$$k_y = (\xi \sin \theta - \eta \cos \theta) \cos \alpha - \zeta \sin \alpha$$

$$k_z = (\xi \sin \theta - \eta \cos \theta) \sin \alpha + \zeta \cos \alpha \quad (28)$$

A reconstruction function at the angle θ is obtained as in the following Equation (29).

[Math. 47]

$$\rho(x, y, z, \theta) = \frac{1}{(2\pi)^2} \int_{-\infty}^{\infty}\int_{-\infty}^{\infty}\int_{-\infty}^{\infty} e^{i(\xi X + \eta Y + \zeta Z)} \tilde{\phi}_R(k_y, k, \theta)\left(\frac{dk}{dk_z}\right) d\xi d\eta d\zeta \quad (29)$$

$$k = \frac{1}{2}\sqrt{k_x^2 + k_y^2 + k_z^2} = \frac{1}{2}\sqrt{\xi^2 + \eta^2 + \zeta^2}$$

$$\frac{dk}{dk_z} = \frac{k_z}{2\sqrt{k_x^2 + k_y^2 + k_z^2}} = \frac{(\xi \sin \theta - \eta \cos \theta) \sin \alpha + \zeta \cos \alpha}{2\sqrt{\xi^2 + \eta^2 + \zeta^2}}$$

Here, $k_x$, $k_y$, $k_z$, and the like are functions of ξ, η, and ζ as in Equations (26) and (28), and thus data in local coordinates of the angle θ can be transformed into the whole coordinates by using only Fourier transform.
Finally, a reconstructed image, that is, an imaging function as shown in Equation (30) is obtained through integration with respect to the angle θ.

[Math. 48]

$$P(X, Y, Z) = \int_0^{2\pi} \rho(x, y, z, \theta) d\theta \qquad (30)$$

$$= \frac{1}{(2\pi)^2} \int_0^{2\pi} \int_{-\infty}^{\infty} \int_{-\infty}^{\infty} \int_{-\infty}^{\infty} e^{i(\xi X - \eta Y + \zeta Z)} \tilde{\phi}_k(k_y, k, \theta)$$

$$\left(\frac{dk}{dk_z}\right) d\xi d\eta d\zeta d\theta$$

$$k_y = (\xi \sin\theta - \eta \cos\theta)\cos\alpha - \zeta \sin\alpha$$

$$k = \frac{1}{2}\sqrt{k_x^2 + k_y^2 + k_z^2} = \frac{1}{2}\sqrt{\xi^2 + \eta^2 + \zeta^2}$$

$$\frac{dk}{dk_z} = \frac{k_z}{2\sqrt{k_x^2 + k_y^2 + k_z^2}}$$

$$= \frac{(\xi \sin\theta - \eta \cos\theta)\sin\alpha + \zeta \cos\alpha}{2\sqrt{\xi^2 + \eta^2 + \zeta^2}}$$

It is possible to reconstruct an image regarding internal information of an object by using the imaging function.

<Reconstructed Image Obtained in Examination Apparatus>

A description will be made of an effect of obtaining a reconstructed image in the mammography apparatus 1 described above.

The mammography apparatus 1 according to the present embodiment is effective in observation of defective tissue in, especially, the breast.

As a method of observing defective tissue in the breast, in the related art, there is an observation method using an X-ray, an ultrasonic wave, or MRI, but, observation using an X-ray has a problem that the type of organic tissue is hard to identify by using an X-ray, and thus the X-ray is not suitable for observation of defective tissue in the breast. Observation using an ultrasonic wave has a problem that an ultrasonic wave is greatly attenuated in the lipid occupying the large part of a region, thus it is hard to improve S/N of a constructed image, and therefore the ultrasonic wave is not suitable for observation of defective tissue in the breast. Observation using MRI has a problem that a contrast agent is necessary, a clear constructed image is obtained, but defective tissue is hard to identify from the constructed image, and thus MRI is not suitable for observation of defective tissue in the breast. A superconducting coil and a cooling system thereof which are required to generate a strong magnetic field are large-sized, and expensive.

In contrast, an ultra-wideband (UWB) microwave with 1 to 10 GHz is used for observation in the mammography apparatus 1 according to the present embodiment. A microwave is scarcely attenuated in a living body, particularly, the lipid and the like, and thus the microwave is effective in observation of defective tissue in the breast. An apparatus configuration is simpler than MRI, other substances such as a contrast agent is not necessary, and thus the mammography apparatus can be versatilely used. The mammography apparatus 1 according to the present embodiment images a three-dimensional constituent element of the inside of a living body such as the breast on the basis of monostatic scattered wave data of a microwave by using the above-described reverse scattering theory, and thus it is possible to image internal information (configuration) of the living body versatilely and at a high speed.

As an example of a check test for the above-described mammography apparatus 1, for example, observation in a living body model in which a case is filled with alumina balls and observation of the breast of an animal have been performed until now. Hereinafter, an observation result will be described.

Figure 8:
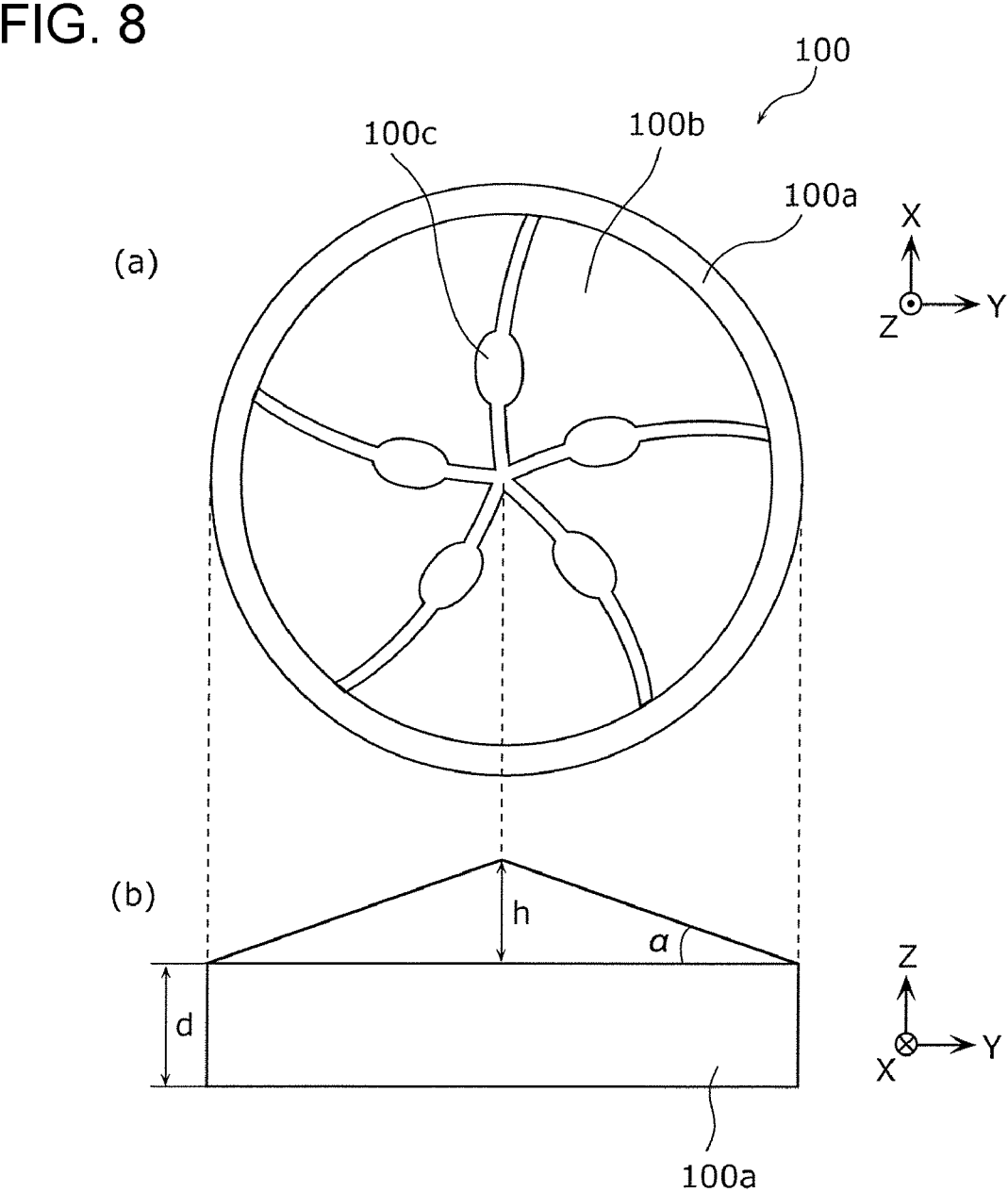
FIG. 8 is a schematic diagram illustrating a test model for a measurement test using the mammography apparatus according to Embodiment 1.
Figure 9:
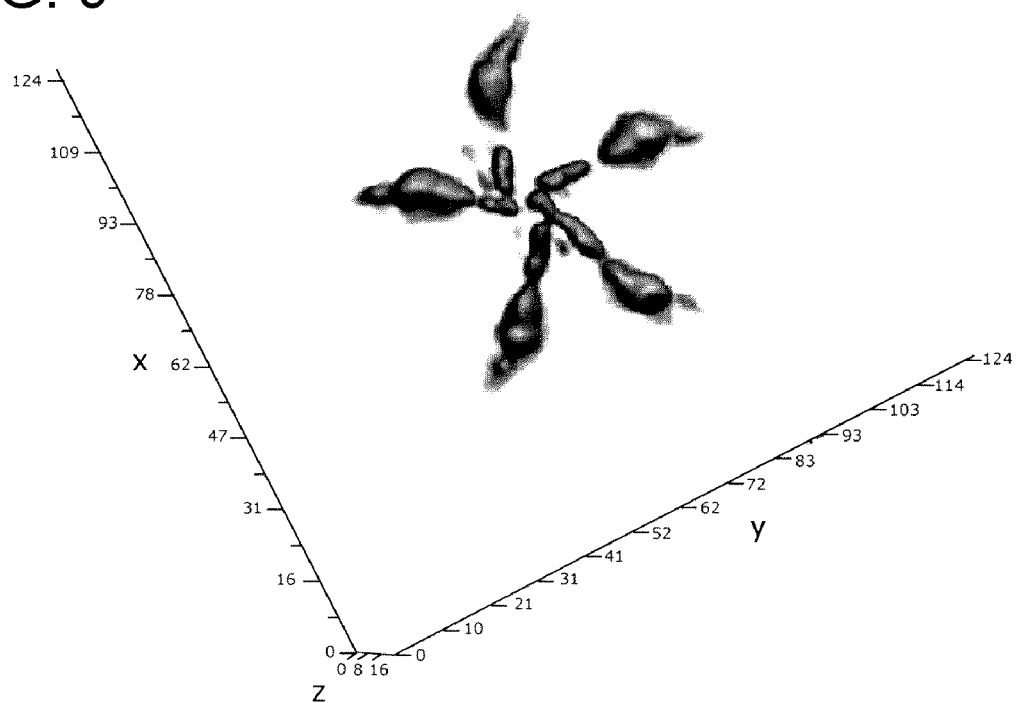
FIG. 9 is a diagram illustrating a measurement result of measuring the test model illustrated in FIG. 8 with the mammography apparatus.

FIG. 8 is a schematic diagram illustrating a test model for a measurement test using the mammography apparatus 1 according to Embodiment 1. FIG. 9 is a diagram illustrating a measurement result of measuring the test model illustrated in FIG. 8 in the mammography apparatus.

The breast of a pig is supposed as a test model 100, as illustrated in FIGS. 8 (a) and 8 (b), alumina balls 100b each of which has a diameter of 1 mm and relative permittivity of 6 fill a plastic container 100a of which an inner diameter is 30 cm, and a height is about 10 cm, and five rubber hoses 100c containing water and each having a section diameter of 5 mm are disposed to be buried in the alumina balls 100b. Specifically, in (b) of FIG. 8, a height d is d=34 mm, a height h is h=54.6 mm, and an angle α is α=20°.

As an example of a measurement condition, a microwave with 10 GHz or less was used as a microwave transmitted from the transmitting antenna. In this case, an antenna of which a size of a portion brought into contact with the test model 100 is about 15 mm×15 mm was as each of the transmitting antenna 36a and the receiving antenna 36b. Under this condition, the test model 100 was observed by the mammography apparatus 1 according to the present embodiment, and, as illustrated in FIG. 9, the five rubber hoses 100c containing water disposed in the test model 100 could be observed. Although not illustrated, the observation could be performed while changing an observation position in the depth direction by changing a frequency of the microwave. In the observation result illustrated in FIG. 9, the rubber hoses 100c containing water were observed at a location of which a depth from the surface is about 54 mm. This observation result is proper for the model in FIG. 8. From the observation result, it was confirmed that a reconstructed image with higher accuracy than that of an image obtained through observation using the above-described X-ray, ultrasonic wave, and MRI is obtained.

As mentioned above, the mammography apparatus 1 according to the present embodiment is effective, especially, in observation of defective tissue in the breast.

As described above, according to the mammography apparatus 1 of the present embodiment, in the analysis model in which the probe 36 is moved linearly along the generating line of the cone 60a, a partial differential equation for inverse problem is set, and an imaging function is obtained by solving the equation. Consequently, in the mammography apparatus 1 according to the present embodiment, it is possible to image internal information of the target object 10 versatilely and at a high speed.

Regarding specific effects, the mammography apparatus 1 according to the present embodiment uses a microwave as a wave, and thus there is no probability of exposure to radiation when an X-ray is radiated to a living body and is safe, compared with an observation method using an X-ray. Since a contrast ratio between cancer tissue and normal tissue is high in an image, it is possible to perform observation with high sensitivity in a short period of time, compared with an observation method using an X-ray. Since observation can be performed in a state in which the probe is brought into contact with an examination target location, it is possible to achieve miniaturization and low cost of an apparatus.

Since image analysis can be performed without depending on subjectivity or a skill of a user, that is, a diagnostician such as a doctor, it is possible to perform accurate diagnosis even in a case where a diagnostician differs.

Since observation can be performed in a state in which the probe is brought into contact with an examination target location without pressing the examination target location, it is possible to easily perform observation in a state in which a patient does not feel pain with clothes.

The above-described calculation formulae and the procedures of deriving the calculation formulae are only examples, and other calculation formulae and other deriving procedures may be used.

In the present embodiment, a microwave is used as a wave, but a wave is not limited to a microwave, and may be an electromagnetic wave with frequencies in other frequency range, and may be an ultrasonic wave. In the present embodiment, since a microwave is used, a periodic wave with a predetermined frequency is used, but a wave is not limited to a periodic wave, and a pulse wave may be used.

In the present embodiment, the breast has been described as an example of a target object, but a target object is not limited to the breast, and may be other living bodies or objects, for example, a conical concrete support.

Embodiment 2

Next, Embodiment 2 of the present invention will be described.

A configuration of a mammography apparatus 1 according to the present embodiment is substantially the same as the configuration of the mammography apparatus 1 according to Embodiment 1, but is different from the mammography apparatus 1 according to Embodiment 1 in that a generating line of a cone in the analysis model of the cone described in Embodiment 1 is curved, and the transmitting antenna element 36a and the receiving antenna element 36b are moved along the curved generating line. Therefore, an image reconstruction algorithm executed in an image reconstruction unit of the mammography apparatus 1 according to the present embodiment is different from that in the mammography apparatus 1 according to Embodiment 1.

In the mammography apparatus 1 according to Embodiment 2, the transmitting antenna element 36a and the receiving antenna element 36b are integrally moved along a line corresponding to a curved generating line of a substantial cone in the target object 10. Here, the "substantial cone" is a cone having a curved generating line, and the "line corresponding to the generating line of the substantial cone" is a line corresponding to a curved generating line of a substantial cone in a case where a shape of a target object 10 is regarded as a substantially conical shape having a curved generating line.

Hereinafter, a description will be made of the image reconstruction algorithm in the mammography apparatus 1 according to the present embodiment.

<Image Reconstruction Algorithm>

Figure 10:
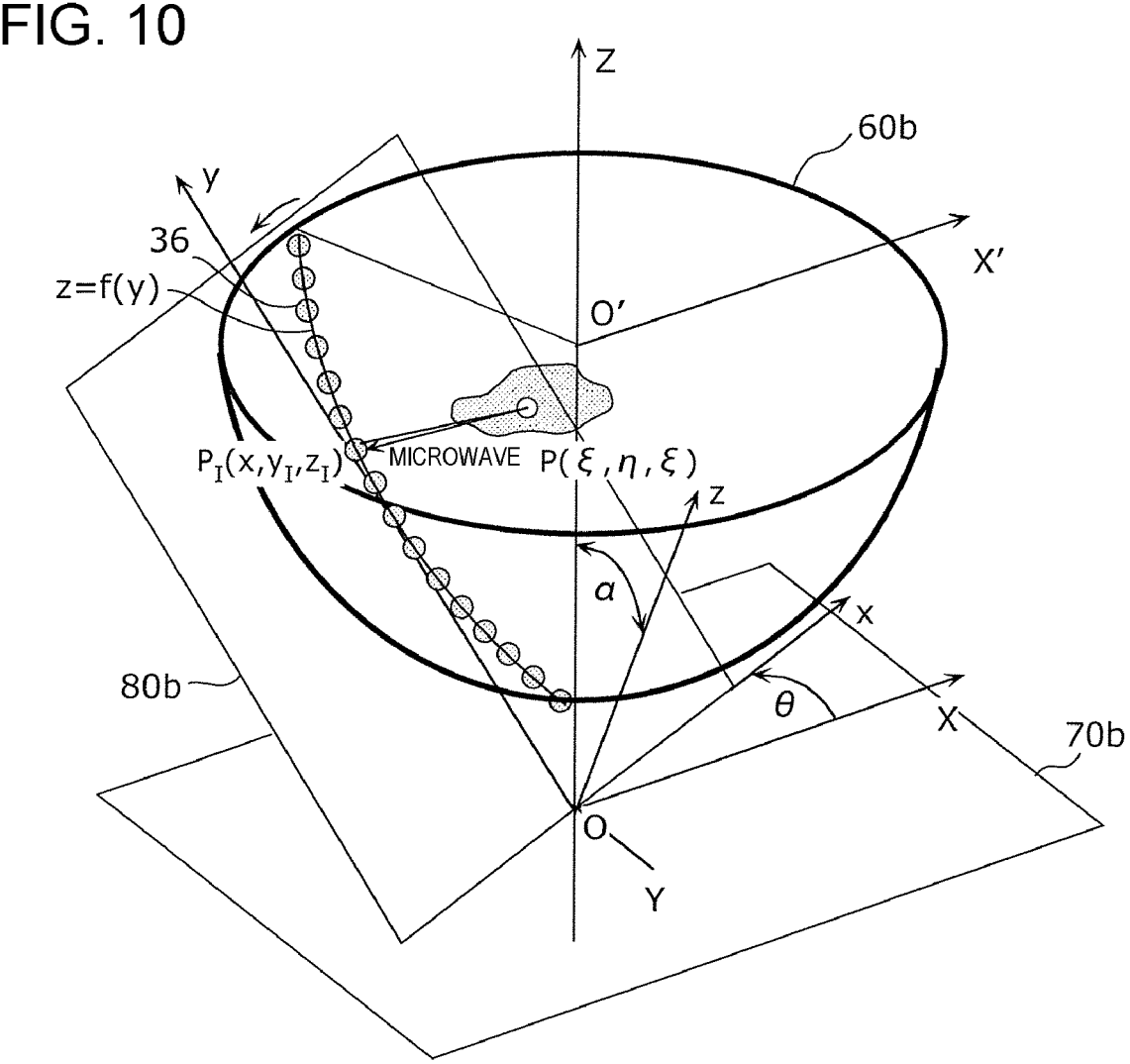
FIG. 10 illustrates an analysis model for explaining a principle of a mammography method according to Embodiment 2.
Figure 11:
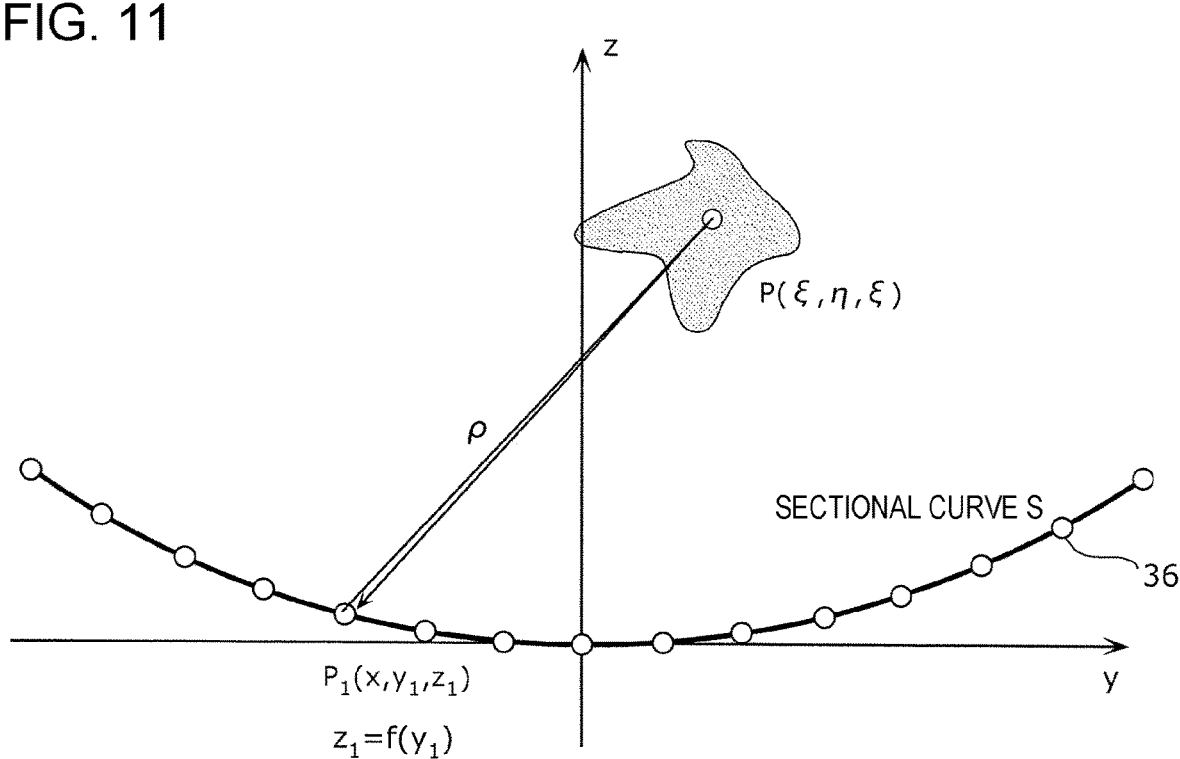
FIG. 11 illustrates an analysis model for explaining a principle of the mammography method according to Embodiment 2.

FIGS. 10 and 11 illustrate analysis models for explaining a principle of a scattering tomography method according to the present embodiment. Hereinafter, a description will be made of derivation of an imaging function in the mammography apparatus according to the present embodiment by using a model illustrated in FIGS. 10 and 11 as an analysis model.

In the image reconstruction algorithm (theory) described below, it is assumed that an imaging target (target object 10) is a cone having a curved generating line, that is, a hemispherical or a dome-like cone. By using the cone as an analysis model, a radiation point (single transmitting antenna element 36a) and a receiving point (single receiving antenna element 36b) of a wave are provided at any positions on the generating line. In other words, an analysis model is formed such that the probe 36 is moved on the generating line of the cone having the curved generating line. In this image reconstruction algorithm, monostatic analysis in which the radiation point and the receiving point are assumed to be located at the same position is performed. Internal information of an imaging target is imaged by using transmission data indicating a radiated wave which is radiated from the radiation point and scattered wave data indicating a scattered wave received at the receiving point.

Specifically, in an analysis model according to the present embodiment, as illustrated in FIG. 10, an imaging target is assumed to be a cone (substantial cone) 60b having a curved generating line. The probe 36 is moved along the generating line of the cone 60b. The probe 36 may be rotationally moved centering on an axis passing through the vertex of the cone 60b and the center of the base of the cone 60b. In other words, measurement is performed while the probe 36 formed of a plurality of transmitting antenna elements 36a and a plurality of receiving antenna elements 36b are being moved linearly in the same direction as an axis of rotational symmetry of the cone 60b used as the analysis model when seen in a plan view from at least one direction. Here, the axis of rotational symmetry of the cone indicates a straight line connecting the vertex of the cone to the center of the base of the cone.

Specifically, it is assumed that a tangential plane 80b of the cone 60b at a position of the probe 36 is supposed, the virtual tangential plane 80b is rotated centering on the axis passing through the vertex of the cone 60b and the center of the base of the cone 60b, and scattered wave data is obtained with respect to all rotation angles 6. A three-dimensional internal structure of the cone 60b is reconstructed on the basis of monostatic time series data in the surface of the cone 60b. A theory thereof will now be described.

In this analysis model, as illustrated in FIG. 10, the vertex of the cone 60b is indicated by a point O, and the center of the circle of the base of the cone 60b is indicated by a point O'. A direction directed from the point O to the point O' is set to a Z direction (Z axis direction). On the side surface of the cone 60b, a plane which is in contact with the cone 60b at a position is set to the tangential plane 80b. A plane which includes a point at which the tangential plane 80b intersects the Z axis and is parallel to the base of the cone 60b is set to a reference plane 70b. Any one direction in the reference plane 70b is set to an X direction (X axis direction), and a direction perpendicular to the X direction in the reference plane 70b is set to a Y direction (Y axis direction).

In the base of the cone 60b, a direction which is parallel to the X direction is set to an X' direction (X' axis direction), and a direction which is parallel to the Y axis direction is set to a Y' direction (Y' axis direction).

One direction of an intersection line at which the tangential plane 80b intersects the reference plane 70b is set to an x direction (x axis direction). In the tangential plane 80b, a direction directed from the point O toward the base of the cone 60b is set to a y direction (y axis direction). A direction perpendicular to the x direction and the y direction is set to a z direction (z axis direction).

In the reference plane 70b, it is assumed that the x axis is rotated centering on the Z axis, and an angle formed between the X axis and the x axis is indicated by θ. An angle formed between the Z axis and the z axis is indicated by α.

FIG. 11 is a partially enlarged schematic diagram of a locus of the probe 36 moved on the generating line of the cone 60b illustrated in FIG. 10. As illustrated in FIG. 11, x and y coordinates are located on a surface of the target object, and a z coordinate is located in a normal direction to the surface of the target object. In the analysis model, the probe 36 is moved to be curved on a curved surface in the xyz space.

In the image reconstruction algorithm according to the present embodiment, in the same manner as in the mammography apparatus 1 according to Embodiment 1, first, a Green's function (reconstruction function) which is necessary for imaging is set. A partial differential equation regarding a three-dimensional space formed of four variables such as (t,x,y,z) of which the function is a solution (function) is built. The partial differential equation is solved by using transmission data radiated from the transmitting antenna element 36a and reception data (scattering data) received by the receiving antenna element 36b as boundary conditions and the strict imaging function is obtained. Consequently, internal information of an object can be imaged with high quality and at a high speed.

Detailed description is as follows.

1. Inverse Problem of Scattering and Green's Function

In FIG. 10, a situation is considered in which a wave emitted from a point $r_1$ is reflected at a point so as to be returned to a point $r_2$. Here, in the mammography apparatus 1 according to the present embodiment, the point $r_1$ and the point $r_2$ are located at the same position. Under the condition that a frequency ω is constant, the transmitting point $r_1$ and the receiving point $r_2$ of a wave are freely moved on the curved surface (a side surface of a cone 60b) while satisfying a certain constraint condition. If data obtained in this case is indicated by $G(r_1,r_2,\omega)$, this function relates to a distribution of reflection points in a region. Here, ω is an angular frequency, and is 2πf. $G(r_1, r_2,\omega)$ is a sum of reflected signals from all points, and, since there are many reflection points in the region, and $G(r_1, r_2,\omega)$ may be regarded in the same manner as in Equation (1) described in Embodiment 1.

However, in the present embodiment, the constraint condition imposed on the transmitting point $r_1$ and the receiving point $r_2$ of a wave is a condition that the point $r_1$ and the point $r_2$ are moved on a certain curved surface, and the point $r_1$ and the point $r_2$ are located at the substantially same position (coordinate).

A description will be made of a theoretical structure of an inverse problem of scattering by using the function $G(r_1,r_2,\omega)$.

2. Monostatic reverse scattering theory on rotationally symmetric curved surface, using cone having curved generating line as analysis model Next, a description will be made of a method of obtaining these differential operators. In the analysis model according to the present embodiment, as illustrated in FIGS. 10 and 11, the generating line of the cone in the analysis model of Embodiment 1 is curved, and the transmitting antenna and the receiving antenna are moved along the curved generating line. The antenna array may be rotationally moved centering on the Z axis. On the curved generating line, x, y, and z coordinates of $r_1$ and $r_2$ are expressed as $r_1=(x,y_1,z_1)$ (=(x, y,z)) and $r_2=(x,y_2,z_2)$ (=(x,y,z)).

Here, the function G is defined in the same manner as in Equation (3) described in Embodiment 1, and an equation satisfied by the function $G(r_1,r_2,\omega)$ is obtained on the basis of $r_1=(x,y_1,z_1)$ and $r_2=(x,y_2,z_2)$. Next, as an equation satisfying the function $G(r_1,r_2,\omega)$, a function φ as in the following Equation (31) is introduced. In addition, φ in Equation (34) corresponds to a reconstruction function (solution) for reconstructing an image regarding internal information of an object in the present invention.

In FIG. 11, regarding a wave radiated from a point $P_1$ on a sectional curve S, reflected at a point P, and then received at the point $P_1$, the function φ may be written as in the following Equation (31). With respect to the vector $r_1$ and the vector $r_2$, a relationship of $r_1=r_2=r(x,y,z)$ is established.

[Math. 49]

$$\varphi(x, y, z) = \int\int_D \frac{e^{ik\rho}}{\rho} \frac{e^{ik\rho}}{\rho} \varepsilon(\xi, \eta, \zeta)d\xi d\eta d\zeta \qquad (31)$$

$$\rho = \sqrt{(x-\xi)^2 + (y-\eta)^2 + (z-\zeta)^2}$$

Here, a time factor is assumed to be proportional to $\exp^{-i\omega t}$, and a wave number is indicated by k. The Kernel function in the integrand term of the above equation is replaced with φ.

[Math. 50]

$$\phi = \frac{e^{ik\rho}}{\rho} \frac{e^{ik\rho}}{\rho} \qquad (32)$$

A partial differential equation having this equation and results of differentiation and integration of the equation with respect to ξ, η, and ζ as solutions is obtained. To do so, high order terms related to 1/ρ generated as a result of differentiation may be disregarded, and calculation may be performed.

Here, shortcuts in differentiation are defined as in the following Expression (33).

[Math. 51]

$$\frac{\partial}{\partial t} \to \partial_t, \frac{\partial}{\partial x} \to \partial_x, \frac{\partial}{\partial y} \to \partial_y, \frac{\partial}{\partial z} \to \partial_z \qquad (33)$$

If differentiation of Φ in each order is obtained by using Expression (33), the following Equation (34) is obtained.

[Math. 52]

$$\partial_x \phi = 2ik\frac{x-\xi}{\rho}\phi + o(\rho^{-3}) \qquad (34)$$

$$\partial_y \phi = 2ik\frac{y-\eta}{\rho}\phi + o(\rho^{-3})$$

$$\partial_z \phi = 2ik\frac{z-\zeta}{\rho}\phi + o(\rho^{-3})$$

$$\partial_x \partial_x \phi = (2ik)^2 \frac{(x-\xi)^2}{\rho^2}\phi + o(\rho^{-3})$$

$$\partial_y \partial_y \phi = (2ik)^2 \frac{(y-\eta)^2}{\rho^2}\phi + o(\rho^{-3})$$

$$\partial_z \partial_z \phi = (2ik)^2 \frac{(z-\zeta)^2}{\rho^2}\phi + o(\rho^{-3})$$

In the following equations, the cumbersome term of o(*) is omitted. Here, * indicates any variable. If a sum of four equations regarding second-order differentiation is taken, the following Equation (35) is obtained.

[Math. 53]

$$\Delta_3 \phi = (\partial_x^2 + \partial_y^2 + \partial_z^2)\phi = (2ik)^2 \phi + o(\rho^{-3}) \tag{35}$$

Therefore, the following equation is obtained.

[Math. 54]

$$\{\Delta_3 - (2ik)^2\}\phi = 0 + o(\rho^{-3}) \tag{36}$$

The equations are summarized, and thus the following Equation (37) is finally obtained. Equation (37) corresponds to a partial differential equation in the present invention.

[Math. 55]

$$\Delta_3 - \frac{1}{(c/2)^2}\frac{\partial^2}{\partial t^2}\phi = 0 \tag{37}$$

A solution of Equation (37) is obtained by assuming that a time factor of $\phi$ is proportional to $\exp^{-i\omega t}$. First, if multiple Fourier transform is performed on $\phi$ with respect to t, x, and y, the following Equation (38) is obtained.

[Math. 56]

$$\tilde{\varphi}(k_x, k_y, z, k) = \int_{-\infty}^{\infty} e^{i\omega t}dt \int_{-\infty}^{\infty} e^{ik_y y}dy \int_{-\infty}^{\infty} e^{ik_x x}\varphi(x, y, z, t)dx \tag{38}$$

If partial differentiations with respect to z is respectively written as $D_z$, the following equation is obtained.

[Math. 57]

$$(D_z^2 - k_x^2 - k_y^2 + 4k^2)\tilde{\varphi} = 0 \tag{39}$$

Here, if the relationship of $\omega$=ck is used to solve the equation, two elementary solutions of the above equation are given as in the following Equation (40).

[Math. 58]

$$E_1 = e^{iz\sqrt{4k^2 - k_x^2 - k_y^2}}$$
$$E_2 = e^{-iz\sqrt{4k^2 - k_x^2 - k_y^2}} \tag{40}$$

Here, taking into consideration that a time factor is $e^{-i\omega t}$, a phase is added in the path of a radiated electric wave, and an electric wave reflected from an object rebounds toward a measurement surface, $E_1$ is only a meaningful solution. Therefore, the solution of Equation (37) may be rewritten as in the following Equation (41) through inverse Fourier transform.

[Math. 59]

$$\tilde{\varphi}(x, y, z, k) = \tag{41}$$
$$\frac{1}{(2\pi)^2}\int_{-\infty}^{\infty}\int_{-\infty}^{\infty} e^{-ik_x x - ik_y y}a(k_x, k_y, k)e^{iz\sqrt{4k^2 - k_x^2 - k_y^2}}dk_x dk_y$$

An equation of the sectional curve S in which x is fixed is assumed to be the following Equation (42).

[Math. 60]

$$z = f(y) \tag{42}$$

A boundary condition given on the sectional curve S is as in the following Equation (43).

[Math. 61]

$$\phi(x, y, f(y), k) = \tag{43}$$
$$\frac{1}{(2\pi)^2}\int_{-\infty}^{\infty}\int_{-\infty}^{\infty} e^{-i(k_x x + k_y y)}a(k_x, k_y, k)e^{if(y)\sqrt{4k^2 - k_x^2 - k_y^2}}dk_x dk_y$$

Here, a solution of the integral equation (43) is obtained. A function $\Phi$ obtained by performing Fourier transform on time series data $\phi(x, y_1, z_1, t)$ measured the point $P_1$ on the curved surface may be written as in the following Equation (44).

[Math. 62]

$$\Phi_I(k_x, y_I, k) = \int_{-\infty}^{\infty}\int_{-\infty}^{\infty} e^{-ikt - ik_x x}\phi(x, y_I, z_I, t)dtdx \tag{44}$$

Here, $z_1$ satisfies the following expression.

[Math. 63]

$$z_I = f(y_I) \tag{45}$$

Since there is no data except for x=0, $\phi$ may be written as follows.

[Math. 64]

$$\phi(x, y_I, z_I, t) = \delta(x)\phi_R(y_I, z_I, t) \tag{46}$$

Then, Equation (44) is given as follows.

[Math. 65]

$$\Phi_I(k_x, y_I, k) = \int_{-\infty}^{\infty}\int_{-\infty}^{\infty} e^{-ikt - ik_x x}\delta(x)\phi_R(y_I, z_I, t)dtdx \tag{47}$$
$$= \int_{-\infty}^{\infty} e^{-ikt}\phi_R(y_i, z_i, t)dt$$

Here, $k_x$ is not included in the right side of Equation (47) However, the right side is expressed by a function like the following Equation (48) by taking into consideration that data about a certain angle $\theta$ is obtained.

[Math. 66]

$$\Psi_I(y_i, k, \theta) = \int_{-\infty}^{\infty} e^{-ikt}\phi_R(y_I, z_I, t)dt \tag{48}$$

This symbol is used, and thus the following Equation (49) is obtained.

[Math. 67]

$$\Psi_I(y_I, k, \theta) = \frac{1}{(2\pi)^2} \int_{-\infty}^{\infty}\int_{-\infty}^{\infty} e^{-i(k_y y)} a_I(k_x, k_y, k) e^{iz_I\sqrt{4k^2-k_x^2-k_y^2}} dk_y \quad (49)$$

Equation (49) is rewritten as the following Equation (50).

[Math. 68]

$$\Psi_I(y_I, k, \theta)\delta(y - y_I)\delta(x) = \quad (50)$$
$$\frac{1}{(2\pi)^2} \int_{-\infty}^{\infty}\int_{-\infty}^{\infty} e^{-i(k_x x + k_y y)} a_I(k_x, k_y, k) e^{iz_I\sqrt{4k^2-k_x^2-k_y^2}} dk_x dk_y$$

If Fourier transform is applied to both sides, the following Equation (51) is obtained.

[Math. 69]

$$\int_{-\infty}^{\infty}\int_{-\infty}^{\infty} e^{i(k'_x x + k'_y y)} \Psi_I(y_I, k, \theta)\delta(y-y_I)\delta(x) dx dy = \int_{-\infty}^{\infty}\int_{-\infty}^{\infty} e^{i(k'_x x + k'_y y)} \quad (51)$$
$$\left\{ \frac{1}{(2\pi)^2} \int_{-\infty}^{\infty}\int_{-\infty}^{\infty} e^{-i(k_x x + k_y y)} a_I(k_x, k_y, k) e^{iz_I\sqrt{4k^2-k_x^2-k_y^2}} dk_x dk_y \right\}$$
$$dxdy$$

[Math. 70]

$$e^{ik'_y y_I} \Psi_I(y_I, k, \theta) = \int_{-\infty}^{\infty}\int_{-\infty}^{\infty} \delta(k'_x - k_x)\delta(k'_y - k_y) a_I(k_x, k_y, k) \quad (52)$$
$$e^{iz_I\sqrt{4k^2-k_x^2-k_y^2}} dk_x dk_y$$
$$= a_I(k'_x, k'_y, k) e^{iz_I\sqrt{4k^2-k'^2_x-k'^2_y}}$$

Here, a $(k_x, k_y, k_z)$ is obtained as in the following Equation (53).

[Math. 71]

$$a_I(k_x, k_y, k) = e^{ik_y y_I} e^{-iz_I\sqrt{4k^2-k_x^2-k_y^2}} \Psi_I(y_I, k, \theta) \quad (53)$$

If a sum is obtained with respect to all I, the following Equation (54) is obtained.

[Math. 72]

$$a_\theta(k_x, k_y, k) = \sum_I e^{ik_y y_I} e^{-iz_I\sqrt{4k^2-k_x^2-k_y^2}} \Psi_I(y_I, k, \theta) \quad (54)$$

A solution of the partial differential equation (37) is obtained as in the following Equation (55).

[Math. 73]

$$\phi(x, y, z, k) = \quad (55)$$
$$\frac{1}{(2\pi)^2}\int_{-\infty}^{\infty}\int_{-\infty}^{\infty} e^{-i(k_x x + k_y y)} a_\theta(k_x, k_y, k) e^{iz\sqrt{4k^2-k_x^2-k_y^2}} dk_x dk_y$$

The equation is further modified, and thus the following Equation (56) is obtained.

[Math. 74]

$$\rho(x, y, z, \theta) = \int_{-\infty}^{\infty} \phi(x, y, z, k) dk \quad (56)$$
$$= \int_{-\infty}^{\infty}\left[ \frac{1}{(2\pi)^2}\int_{-\infty}^{\infty}\int_{-\infty}^{\infty} e^{-i(k_x x + k_y y)} a_\theta(k_x, k_y, k)\right.$$
$$\left. e^{iz\sqrt{4k^2-k_x^2-k_y^2}} dk_x dk_y \right] dk$$
$$= \frac{1}{(2\pi)^2}\int_{-\infty}^{\infty}\int_{-\infty}^{\infty}\int_{-\infty}^{\infty} e^{-i(k_x x + k_y y - k_z z)} a_\theta(k_x, k_y, k)$$
$$\left(\frac{dk}{dk_z}\right) dk_x dk_y dk_z$$
$$k_z = \sqrt{4k^2 - k_x^2 - k_y^2}$$
$$\frac{dk}{dk_z} = \frac{d}{dk_z}\left(\frac{1}{2}\sqrt{k_x^2+k_y^2+k_z^2}\right) = \frac{1}{2}\frac{k_z}{\sqrt{k_x^2+k_y^2+k_z^2}}$$

A result obtained at each angle θ is integrated, and thus a three-dimensional reconstructed image shown in the following Equation (57) is obtained.

[Math. 75]

$$P(X, Y, Z) = \int_0^{2\pi} \rho(x, y, z, \theta) d\theta \quad (57)$$

Next, a result calculated in a tangential space is converted into the whole coordinate (X,Y,Z). If projection of the y axis onto an (X,Y) plane is indicated by y', the following Equation (58) is established.

[Math. 76]

$$y = y'\cos\alpha + Z\sin\alpha \quad (58)$$
$$z = -y'\sin\alpha + Z\cos\alpha$$

An equation for transforming (x,y') into (X,Y) is as in the following Equation (59).

[Math. 77]

$$x = X\cos\theta + Y\sin\theta \quad (59)$$
$$y = -X\cos\alpha\sin\theta + Y\cos\alpha\cos\theta + Z\sin\alpha$$
$$z = X\sin\alpha\sin\theta - Y\sin\alpha\cos\theta + Z\sin\alpha$$

This transform formula is applied to the following Equation (60).

[Math. 78]

$$\rho(x, y, z, \theta) = \frac{1}{(2\pi)^2} \int_{-\infty}^{\infty}\int_{-\infty}^{\infty} e^{-i(k_x x + k_y y)} e^{ik_z z} a_\theta(k_x, k_y, k)\left(\frac{dk}{dk_z}\right) dk_x dk_y dk \quad (60)$$

If the above equations are summarized, the above Equation (60) is rewritten as the following Equation (61).

[Math. 79]

$$\rho(x, y, z, \theta) = \frac{1}{(2\pi)^2}\int_{-\infty}^{\infty}\int_{-\infty}^{\infty} e^{-i\{k_x(X\cos\theta+Y\sin\theta)+k_y(-X\cos\alpha\sin\theta+Y\cos\alpha\cos\theta+Z\sin\alpha)-k_z(X\sin\alpha\sin\theta-Y\sin\alpha\cos\theta+Z\cos\alpha)\}} \cdot a_\theta(k_x, k_y, k)\left(\frac{dk}{dk_z}\right)dk_x dk_y dk = \quad (61)$$

$$\frac{1}{(2\pi)^2}\int_{-\infty}^{\infty}\int_{-\infty}^{\infty} e^{-i\{(k_x\cos\theta-k_y\cos\alpha\sin\theta-k_z\sin\alpha\sin\theta)X+(k_x\sin\theta+k_y\cos\alpha\cos\theta+k_z\sin\alpha\cos\theta)Y+(k_y\sin\alpha-k_z\cos\alpha)Z\}} \cdot a_\theta(k_x, k_y, k)\left(\frac{dk}{dk_z}\right)dk_x dk_y dk$$

In a spectral region, variable transformation (inverse transformation) is performed according to the following Equation (62).

The variables $\xi$, $\eta$, and $\zeta$ used in the following Equations (62) and (63) are not the coordinate $(\xi, \eta, \zeta)$ of the point P used in FIG. 10, Equation (31) and the like, and are new variables for variable transformation.

[Math. 80]

$$\xi = -k_x\cos\theta + (k_y\cos\alpha + k_z\sin\alpha)\sin\theta \quad (62)$$
$$\eta = -k_x\sin\theta - (k_y\cos\alpha + k_z\sin\alpha)\cos\theta$$
$$\zeta = -k_y\sin\alpha + k_z\cos\alpha$$

Inverse transform is according to the following Equation (63)

[Math. 81]

$$k_x = -\xi\cos\theta - \eta\sin\theta \quad (63)$$
$$k_y = (\xi\sin\theta - \eta\cos\theta)\cos\alpha - \zeta\sin\alpha$$
$$k_z = (\xi\sin\theta - \eta\cos\theta)\sin\alpha + \zeta\cos\alpha$$

A reconstruction function at the angle $\theta$ is obtained as in the following Equation (64).

[Math. 82]

$$\rho(x, y, z, \theta) = \quad (64)$$
$$\frac{1}{(2\pi)^2}\int_{-\infty}^{\infty}\int_{-\infty}^{\infty}\int_{-\infty}^{\infty} e^{i(\xi X+\eta Y+\zeta Z)} a_\theta(k_x, k_y, k)\left(\frac{dk}{dk_z}\right)d\xi d\eta d\zeta$$

Here, the function in the integrand term is given as in the following Equation (65).

[Math. 83]

$$a_\theta(k_x, k_y, k) = \sum_l e^{ik_{y_1} y_l} e^{-if(y_l)\sqrt{4k^2-k_x^2-k_y^2}} \Psi_l(y_l, k, \theta) \quad (65)$$

Here, $k_x$, $k_y$, and $k_z$ are functions of $\xi$, $\eta$, and $\zeta$ as in Equation (28), and thus data in local coordinates of the angle $\theta$ can be transformed into the whole coordinates by using only Fourier transform. The following Equation (66) is used for transform into the whole coordinates. That is, finally, an imaging function is obtained through integration with respect to the angle $\theta$.

[Math. 84]

$$P(X, Y, Z) = \int_0^{2\pi} \rho(x, y, z, \theta) d\theta \quad (66)$$

An image regarding internal information of the target object 10 is reconstructed by using the imaging function. Therefore, it is possible to generate an image regarding internal information of the target object 10 such as an internal defect and the like of the target object 10 versatilely and at a high speed. In the step of reconstructing an image, the function $\phi$ is set in a three-dimensional space, and thus it is possible to image internal information of the target object 10 having a curved surface with a large curvature with higher accuracy and at a high speed.

As mentioned above, in the mammography apparatus according to the present embodiment, a partial differential equation for inverse problem is set in an analysis model in which the probe 36 is moved to be curved on a curved surface, and an imaging function is obtained by solving the equation. Consequently, in the mammography apparatus analyzing a scattered wave of a wave radiated to a living body which is a target object, it is possible to image internal information of a target object having a curved surface with a large curvature versatilely and at a high speed.

Embodiment 3

Next, a description will be made of Embodiment 3. A mammography apparatus according to the present embodiment is different from the mammography apparatus 1 according to Embodiment 1 in that a target object having an asymmetric conical shape is used as an analysis model.

In the mammography apparatus 1 according to Embodiment 3, the transmitting antenna element 36a and the receiving antenna element 36b are integrally moved along a line corresponding to a generating line of an asymmetric pyramid in the target object 10. Here, the "line corresponding to the generating line of the asymmetric pyramid" is a line corresponding to a generating line of a pyramid in a case where a shape of a target object 10 is regarded as an asymmetric pyramidal shape.

In a case where a living body is an observation target, a shape of the living body partially matches a shape of a cone or a shape of a substantial cone having a rotationally symmetric shape, such as the analysis models described in Embodiments 1 and 2, but may not completely match these shapes. In this case, an analysis model in the mammography apparatus 1 according to the present embodiment may be used.

Figure 12:
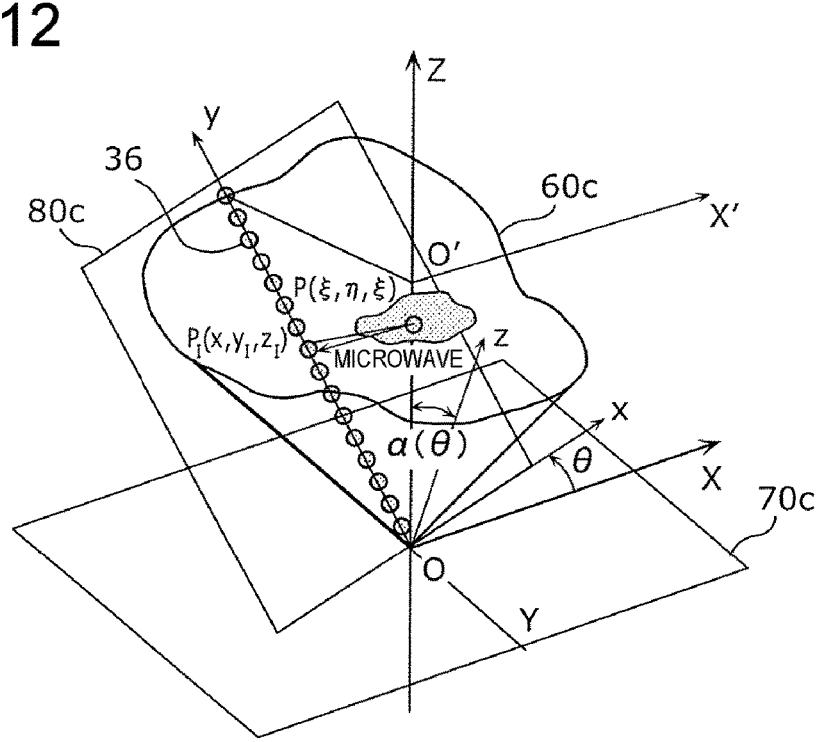
FIG. 12 illustrates an analysis model for explaining a principle of a mammography method according to Embodiment 3.

Hereinafter, a description will be made of the mammography apparatus using a rotationally asymmetric pyramid as an analysis model. FIG. 12 illustrates an analysis model for explaining a principle of a scattering tomography method according to the present embodiment.

An image reconstruction algorithm of the mammography apparatus according to the present embodiment is substantially the same as the image reconstruction algorithm of the mammography apparatus according to Embodiment 1, but is different from that of the mammography apparatus 1 according to Embodiment 1 in that the angle α in the analysis model illustrated in FIG. 2 depends on the rotation angle θ of the generating line. In other words, the target object 10 has a rotationally asymmetric pyramidal shape, and also has a shape of which a part is omitted.

Hereinafter, a description will be made of only a difference from the mammography apparatus 1 according to Embodiment 1 in the image reconstruction algorithm.

With respect to Equation (26) described in Embodiment 1, a variable transform formula used for variable transformation in the spectral region and an inverse transform formula thereof are expressed in the following Equation (67).

[Math. 85]

$$\xi = -k_x\cos\theta + \{k_y\cos\alpha(\theta) + k_z\sin\alpha(\theta)\}\sin\theta \quad (67)$$
$$\eta = -k_x\sin\theta - \{k_y\cos\alpha(\theta) + k_z\sin\alpha(\theta)\}\cos\theta$$
$$\varsigma = -k_y\sin\alpha(\theta) + k_z\cos\alpha(\theta)$$
$$k_x = -\xi\cos\theta - \eta\sin\theta$$
$$k_y = (\xi\sin\theta - \eta\cos\theta)\cos\alpha(\theta) - \varsigma\sin\alpha(\theta)$$
$$k_z = (\xi\sin\theta - \eta\cos\theta)\sin\alpha(\theta) + \varsigma\cos\alpha(\theta)$$

A reconstruction function at the angle θ is obtained as in the following Equation (68).

[Math. 86]

$$\rho(x, y, z, \theta) = \quad (68)$$
$$\frac{1}{(2\pi)^2}\int_{-\infty}^{\infty}\int_{-\infty}^{\infty}\int_{-\infty}^{\infty}e^{i(\xi X + \eta Y + \varsigma Z)}\tilde{\phi}_R(k_y, k, \theta)\left(\frac{dk}{dk_z}\right)d\xi d\eta d\varsigma$$
$$k = \frac{1}{2}\sqrt{k_x^2 + k_y^2 + k_z^2} = \frac{1}{2}\sqrt{\xi^2 + \eta^2 + \varsigma^2}$$
$$\frac{dk}{dk_z} = \frac{k_z}{2\sqrt{k_x^2 + k_y^2 + k_z^2}} = \frac{(\xi\sin\theta - \eta\cos\theta)\sin\alpha + \varsigma\cos\alpha}{2\sqrt{\xi^2 + \eta^2 + \varsigma^2}}$$

Here, $k_x$, $k_y$, and $k_z$ are functions of ξ, η, and ς, and thus data in local coordinates of the angle θ can be transformed into the whole coordinates by using only Fourier transform. Finally, a reconstructed image shown in Equation (69) is obtained through integration using the angle θ.

[Math. 87]

$$P(X, Y, Z) = \int_0^{2\pi}\rho(x, y, z, \theta)d\theta \quad (69)$$

As mentioned above, according to the mammography apparatus according to the present embodiment, even in a case where a shape of a living body which is an observation target does not completely match a shape of a cone or a shape of a substantial cone having a rotationally symmetric shape, a partial differential equation for inverse problem is set, and an imaging function can be obtained by solving the equation. Consequently, in the mammography apparatus analyzing a scattered wave of a wave radiated to an object, even in a case where a target object is flexible or is not a perfect cone or a substantial cone, it is possible to image internal information of the target object versatilely and at a high speed.

In the above-described embodiment, the analysis model obtained by omitting a part of the analysis model of the pyramid described in Embodiment 1 has been described as an example, but an analysis model by omitting a part of the analysis model of the pyramid described in Embodiment 2 may be used. Also in this case, an imaging function can be obtained by changing a variable transform formulae used for variable transformation in the spectral region and an inverse transform formula thereof with respect to the equations in the same manner as in the image reconstruction algorithm in the analysis model of the mammography apparatus according to the present embodiment.

Modification Examples and the Like

As mentioned above, the examination apparatus and the examination method according to the present invention have been described on the basis of a plurality of embodiments by exemplifying mammography, but the present invention is not limited to the embodiments. The present invention also includes a form obtained by applying modifications of which a person skilled in the art conceives to the embodiments, and other forms realized by combining any constituent elements in the plurality of embodiments with each other.

For example, in the embodiments, the mammography has been described as an example, and thus a living body, specifically, the breast has been described as an example of a target object, but a target object is not limited to the breast, and may be structures of other living bodies. A target object is not limited to a living body, and may be structures of objects other than a living body. For example, a target object may be a structure such as a conical concrete support. In this case, an analysis model appropriate for a shape of a target object may be built as appropriate.

In the present embodiment, a microwave was used as a wave, but a wave is not limited to a microwave, and electromagnetic waves with frequencies in other frequency range or an ultrasonic wave. In the present embodiment, since a microwave is used, a periodic wave with a predetermined frequency is used, but a wave is not limited to a periodic wave, and a pulse wave may be used.

The above-described calculation formulae and the procedures of deriving the calculation formulae are only examples, and other calculation formulae and other deriving procedures may be used.

In the examination apparatus, a specific processing unit may perform a process performed by another processing unit. In the examination apparatus, an order of performing processes may be changed, and a plurality of processes may be performed in parallel.

A step of observing internal information of a target object in the examination apparatus of the present invention may be executed by a computer. The present invention can be realized as a program for causing a computer to execute steps included in the scattering tomography method. The present invention can be realized as a non-transitory computer readable recording medium such as a CD-ROM on which the program is recorded.

A plurality of constituent elements included in the examination apparatus may be realized as an LSI which is an integrated circuit. The constituent elements may be separately formed as one chip, and some or all thereof may be included in one chip. Here, an LSI is mentioned, but may be called an integrated circuit (IC), a system LSI, a super LSI, or an ultra LSI depending on a difference in the degree of integration.

A technique for an integrated circuit is not limited to an LSI, and may be realized by a dedicated circuit or a general purpose processor. A field programmable gate array (FPGA) which is programmable or a reconfigurable processor in which connection and setting of circuit cells of the LSI inside can be reconstruct may be used.

In a case where a technique for an integrated circuit replacing the LSI will appear with the advance of a semiconductor technique or a separate technique derived therefrom, the constituent elements included in the mammography apparatus may be naturally formed as integrated circuits by using the technique.

As mentioned above, the embodiments of the present invention have been described with reference to the drawings, but are only examples of the present invention, and various configurations other than the above-described configurations may be employed.

Hereinafter, examples of reference embodiments are added.

1-1. An examination method of examining an internal state of a target object by analyzing a scattered wave of a wave radiated to the target object, the method including:

a step of radiating a wave to the target object with a transmitting antenna element which is brought into contact with the target object and radiates the wave to the target object; a step of receiving a scattered wave with a receiving antenna element which is provided integrally with the transmitting antenna element, and is brought into contact with the target object so as to receive the scattered wave as a result of the wave transmitted from the transmitting antenna element being scattered at the target object; and a step of reconstructing an image regarding internal information of the target object on the basis of scattered wave data indicating the scattered wave received by the receiving antenna element, in which, in the step of reconstructing the image, a reconstruction function for reconstructing the image regarding the internal information of the target object is set in a three-dimensional space having the same shape as a shape of the target object, a partial differential equation satisfied by an asymptotic expression of the reconstruction function is built, an imaging function is derived from the scattered wave data by solving the partial differential equation, and the image regarding the internal information of the target object is reconstructed by using the imaging function.

1-2. The examination method according to 1-1.,
in which the target object has a conical shape, and
in which the transmitting antenna element and the receiving antenna element are integrally moved along a generating line of a cone of the target object.

1-3. The examination method according to 1-1.,
in which the target object has a substantially conical shape having a curved generating line, and
in which the transmitting antenna element and the receiving antenna element are integrally moved along the curved generating line.

1-4. The examination method according to 1-1.,
in which the target object has an asymmetric pyramidal shape, and
in which the transmitting antenna element and the receiving antenna element are integrally moved along a generating line of the asymmetric pyramidal shape.

1-5. The examination method according any one of 1-1. to 1-4.,
in which the wave is a microwave.

1-6. The examination method according any one of 1-1. to 1-4.,
in which the wave is a pulse wave or a periodic wave with a predetermined frequency.

2-1. An examination apparatus of examining an internal state of a target object by analyzing a scattered wave of a wave radiated to the target object, the apparatus including:

a transmitting antenna element that is brought into contact with the target object and radiates the wave to the target object;

a receiving antenna element that is provided integrally with the transmitting antenna element, and is brought into contact with the target object so as to receive the scattered wave as a result of the wave radiated from the transmitting antenna element being scattered at the target object; and an image reconstruction unit that reconstructs an image regarding internal information of the target object on the basis of scattered wave data indicating the scattered wave received by the receiving antenna element, wherein the image reconstruction units
sets a reconstruction function for reconstructing the image regarding the internal information of the target object in a three-dimensional space having the same shape as a shape of the target object, builds a partial differential equation satisfied by an asymptotic expression of the reconstruction function, derives an imaging function from the scattered wave data by solving the partial differential equation, and reconstructs the image regarding the internal information of the target object by using the imaging function.

2-2. The examination apparatus according to 2-1.,
in which the target object has a conical shape, and
in which the transmitting antenna element and the receiving antenna element are integrally moved along a generating line of a cone of the target object.

2-3. The examination apparatus according to 2-1.,
in which the target object has a substantially conical shape having a curved generating line, and
in which the transmitting antenna element and the receiving antenna element are integrally moved along the curved generating line.

2-4. The examination apparatus according to 2-1.,
in which the target object has an asymmetric pyramidal shape, and
in which the transmitting antenna element and the receiving antenna element are integrally moved along a generating line of the asymmetric pyramidal shape.

2-5. The examination apparatus according any one of 2-1. to 2-4.,
in which the wave is a microwave.

2-6. The examination apparatus according any one of 2-1. to 2-4.,
in which the wave is a pulse wave or a periodic wave with a predetermined frequency.

INDUSTRIAL APPLICABILITY the examination apparatus and the examination method according to the present invention are useful for examination of a target object having a flexible shape, and are applicable to, for example, a medical apparatus such as a mammography apparatus.

This application is based upon and claims the benefit of priority from Japanese Patent Application No. 2015-192216, filed Sep. 29, 2015; the entire contents of which are incorporated herein by reference.

The invention claimed is:

1. An imaging method comprising:
a step of radiating a wave to a target object;
a step of receiving a scattered wave as a result of the wave being scattered at the target object; and
a step of reconstructing an image regarding internal information of the target object on the basis of scattered wave data indicating the scattered wave,
wherein, in the step of reconstructing the image,
a reconstruction function for reconstructing the image regarding the internal information of the target object is derived by solving a partial differential equation by using the scattered wave data and an analysis model indicating a shape,
an imaging function which is a limiting value of a time variable of the reconstruction function is derived, and
the image regarding the internal information of the target object is reconstructed by using the reconstruction function,
wherein the partial differential equation is
an equation satisfied by the reconstruction function,
expressed by using independent variables indicating positions of a transmitting point and a receiving point which are located at the same position in the target object, and
a linear partial differential equation having, as a solution, a scattering field function which is a function of a field where the scattered wave is generated at each point in a space having the same order as the number of the independent variables,
wherein, in the step of radiating and the step of receiving, a transmitting antenna element radiating the wave to the target object and a receiving antenna element receiving the scattered wave are moved in a pair, and
wherein scattering tomography according to a monostatic method is used in the imaging method.

2. The imaging method according to claim 1,
Wherein the shape indicated by the analysis model is a shape of a cone,
wherein the imaging function is expressed by the following Equation (A), and
wherein, in the step of reconstructing the image, the image regarding the internal information of the target object is reconstructed by using a function expressed by the following Equation (B) which is obtained by integrating the imaging function with respect to θ:

[Math. 1]

$$\rho(x, y, z, \theta) = \int_{-\infty}^{\infty} \phi(x, y, z, k)dk \qquad (A)$$

$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)$$

$$\left(\frac{dk}{dk_z}\right) dk_x dk_y dk_z$$

[Math. 2]

$$P(X, Y, Z) = \int_0^{2\pi} \rho(x, y, z, \theta)d\theta \qquad (B)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the cone is set to the origin, a direction directed from the origin toward the center of a base of the cone is set to a Z direction, a direction passing through the origin in parallel to the base is set to an X direction, and a direction passing through the origin in parallel to the base and orthogonal to the X direction is set to a Y direction; ρ is a function of permittivity; φ is the reconstruction function; $\phi_R$ is a function satisfying $\phi(x,y,0,k)=\phi_R(y,k)\delta(x)$; $k_x$, $k_y$, and $k_z$ are respectively x, y and z components of a wave number; k is a time wave number; and θ is a rotation angle with an axis of the cone as a rotation axis.

3. The imaging method according to claim 2,
wherein the transmitting antenna element and the receiving antenna element are integrally moved along a line corresponding to a generating line of a cone in the target object.

4. The imaging method according to claim 1,
wherein the shape indicated by the analysis model is a shape of a substantial cone having a curved generating line,
wherein the imaging function is expressed by the following Equation (C), and
wherein, in the step of reconstructing the image, the image regarding the internal information of the target object is reconstructed by using a function expressed by the following Equation (D) which is obtained by integrating the imaging function with respect to θ:

[Math. 3]

$$\rho(x, y, z, \theta) = \int_{-\infty}^{\infty} \phi(x, y, z, k)dk \qquad (C)$$

$$= \int_{-\infty}^{\infty} \left[ \frac{1}{(2\pi)^2} \int_{-\infty}^{\infty}\int_{-\infty}^{\infty} e^{-i(k_x x + k_y y)} \right.$$

$$\left. a_\theta(k_x, k_y, k) e^{iz\sqrt{4k^2 - k_x^2 - k_y^2}} dk_x dk_y \right] dk$$

$$= \frac{1}{(2\pi)^2} \int_{-\infty}^{\infty}\int_{-\infty}^{\infty}\int_{-\infty}^{\infty} e^{-i(k_x x + k_y y - k_z z)}$$

$$a_\theta(k_x, k_y, k)\left(\frac{dk}{dk_z}\right) dk_x dk_y dk_z$$

$$k_z = \sqrt{4k^2 - k_x^2 - k_y^2}$$

$$\frac{dk}{dk_z} = \frac{d}{dk_z}\left(\frac{1}{2}\sqrt{k_x^2 + k_y^2 + k_z^2}\right) = \frac{1}{2}\frac{k_z}{\sqrt{k_x^2 + k_y^2 + k_z^2}}$$

-continued

[Math. 4]

$$P(X, Y, Z) = \int_0^{2\pi} \rho(x, y, z, \theta) d\theta \quad (D)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the substantial cone is set to the origin, a direction directed from the origin toward the center of a base of the substantial cone is set to a Z direction, a direction passing through the origin in parallel to the base is set to an X direction, and a direction passing through the origin in parallel to the base and orthogonal to the X direction is set to a Y direction; $\rho$ is a function of permittivity; $\phi$ is the reconstruction function; $a_\theta$ is a coefficient; $k_x$, $k_y$, and $k_z$ are respectively x, y and z components of a wave number; k is a time wave number; and $\theta$ is a rotation angle with an axis of the substantial cone as a rotation axis.

5. The imaging method according to claim 4,
wherein the transmitting antenna element and the receiving antenna element are integrally moved along a line corresponding to a curved generating line of a substantial cone in the target object.

6. The imaging method according to claim 1,
wherein the shape indicated by the analysis model is a shape of an asymmetric pyramid,
wherein the imaging function is expressed by the following Equation (F) in a case where each of $\xi$, $\eta$, and $\zeta$ is a variable satisfying the following Equation (E), and
wherein, in the step of reconstructing the image, the image regarding the internal information of the target object is reconstructed by using a function expressed by the following Equation (G) which is obtained by integrating the imaging function with respect to $\theta$:

[Math. 5]

$$\xi = -k_x \cos\theta + \{k_y \cos\alpha(\theta) + k_z \sin\alpha(\theta)\}\sin\theta \quad (E)$$
$$\eta = -k_x \sin\theta - \{k_y \cos\alpha(\theta) + k_z \sin\alpha(\theta)\}\cos\theta$$
$$\zeta = -k_y \sin\alpha(\theta) + k_z \cos\alpha(\theta)$$
$$k_x = -\xi\cos\theta - \eta\sin\theta$$
$$k_y = (\xi\sin\theta - \eta\cos\theta)\cos\alpha(\theta) - \zeta\sin\alpha(\theta)$$
$$k_z = (\xi\sin\theta - \eta\cos\theta)\sin\alpha(\theta) + \zeta\cos\alpha(\theta)$$

[Math. 6]

$$\rho(x, y, z, \theta) = \quad (F)$$

$$\frac{1}{(2\pi)^2} \int_{-\infty}^{\infty}\int_{-\infty}^{\infty}\int_{-\infty}^{\infty} e^{i(\xi X + \eta Y + \zeta Z)} \tilde{\phi}_R(k_y, k, \theta)\left(\frac{dk}{dk_z}\right) d\xi d\eta d\zeta$$

$$k = \frac{1}{2}\sqrt{k_x^2 + k_y^2 + k_z^2} = \frac{1}{2}\sqrt{\xi^2 + \eta^2 + \zeta^2}$$

$$\frac{dk}{dk_z} = \frac{k_z}{2\sqrt{k_x^2 + k_y^2 + k_z^2}} = \frac{(\xi\sin\theta - \eta\cos\theta)\sin\alpha + \zeta\cos\alpha}{2\sqrt{\xi^2 + \eta^2 + \zeta^2}}$$

[Math. 7]

$$P(X, Y, Z) = \int_0^{2\pi} \rho(x, y, z, \theta) d\theta \quad (G)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the pyramid is set to the origin, a direction directed from the origin toward the center of a base of the pyramid is set to a Z direction, a direction passing through the origin in parallel to the base is set to an X direction, and a direction passing through the origin in parallel to the base and orthogonal to the X direction is set to a Y direction; $\rho$ is a function of permittivity; $\phi$ is the reconstruction function; $\phi_R$ is a function satisfying $\phi(x,y,0,k)=\phi(y,k)\delta(x)$; $a_\theta$ is a coefficient; $k_x$, $k_y$, and $k_z$ are respectively x, y and z components of a wave number; k is a time wave number; $\theta$ is a rotation angle with an axis of the pyramid as a rotation axis; and $\alpha$ is an inclined angle with the Z direction as a reference.

7. The imaging method according to claim 6,
wherein the transmitting antenna element and the receiving antenna element are integrally moved along a line corresponding to a generating line of an asymmetric pyramid in the target object.

8. The imaging method according to claim 1,
wherein, in the radiating step, the wave is radiated to the target object by using a probe in which the receiving antenna element and the transmitting antenna element are integrally provided, and an electric wave absorbing portion is located between the receiving antenna element and the transmitting antenna element, and
wherein, in the receiving step, the scattered wave is received by using the probe.

9. The imaging method according to claim 1,
wherein the wave is a microwave.

10. The imaging method according to claim 1,
wherein the wave is a pulse wave or a periodic wave with a predetermined frequency.

11. An imaging apparatus comprising:
a transmitting antenna element that radiates a wave to a target object;
a receiving antenna element that receives a scattered wave as a result of the wave radiated from the transmitting antenna element being scattered at the target object; and
an image reconstruction unit that reconstructs an image regarding internal information of the target object on the basis of scattered wave data indicating the scattered wave received by the receiving antenna element,
wherein the image reconstruction unit
derives a reconstruction function for reconstructing the image regarding the internal information of the target object by solving a partial differential equation by using the scattered wave data and an analysis model indicating a shape,
derives an imaging function which is a limiting value of a time variable of the reconstruction function, and
reconstructs the image regarding the internal information of the target object by using the reconstruction function,
wherein the partial differential equation is
an equation satisfied by the reconstruction function,
expressed by using independent variables indicating positions of a transmitting point and a receiving point which are located at the same position in the target object, and a linear partial differential equation having, as a solution, a scattering field function which is a function of a field where the scattered wave is generated at each point in a space having the same order as the number of the independent variables, wherein the transmitting antenna element and the receiving antenna element are integrally moved, and wherein scattering tomography according to a monostatic method is used in the imaging apparatus.

12. The imaging apparatus according to claim 11, wherein the shape indicated by the analysis model is a shape of a cone, wherein the imaging function is expressed by the following Equation (A), and wherein the image reconstruction unit reconstructs the image regarding the internal information of the target object by using a function expressed by the following Equation (B) which is obtained by integrating the imaging function with respect to θ:

[Math. 8]

$$\rho(x, y, z, \theta) = \int_{-\infty}^{\infty} \phi(x, y, z, k)dk \quad (A)$$

$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)$$

$$\left(\frac{dk}{dk_z}\right) dk_x dk_y dk_z$$

[Math. 9]

$$P(X, Y, Z) = \int_0^{2\pi} \rho(x, y, z, \theta)d\theta \quad (B)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the cone is set to the origin, a direction directed from the origin toward the center of a base of the cone is set to a Z direction, a direction passing through the origin in parallel to the base is set to an X direction, and a direction passing through the origin in parallel to the base and orthogonal to the X direction is set to a Y direction; ρ is a function of permittivity; φ is the reconstruction function; $\phi_R$ is a function satisfying $\phi(x,y,0,k)=\phi_R(y,k)\delta(x)$; $k_x$, $k_y$, and $k_z$ are respectively x, y and z components of a wave number; k is a time wave number; and θ is a rotation angle with an axis of the cone as a rotation axis.

13. The imaging apparatus according to claim 12, wherein the transmitting antenna element and the receiving antenna element are integrally moved along a line corresponding to a generating line of a cone in the target object.

14. The imaging apparatus according to claim 11, wherein the shape indicated by the analysis model is a shape of a substantial cone having a curved generating line, wherein the imaging function is expressed by the following Equation (C), and wherein the image reconstruction unit reconstructs the image regarding the internal information of the target object by using a function expressed by the following Equation (D) which is obtained by integrating the imaging function with respect to θ:

[Math. 10]

$$\rho(x, y, z, \theta) = \int_{-\infty}^{\infty} \phi(x, y, z, k)dk \quad (C)$$

$$= \int_{-\infty}^{\infty} \left[\frac{1}{(2\pi)^2} \int_{-\infty}^{\infty}\int_{-\infty}^{\infty} e^{-i(k_x x + k_y y)} a_\theta(k_x, k_y, k)\right.$$

$$\left. e^{iz\sqrt{4k^2 - k_x^2 - k_y^2}} dk_x dk_y \right] dk$$

$$= \frac{1}{(2\pi)^2} \int_{-\infty}^{\infty}\int_{-\infty}^{\infty}\int_{-\infty}^{\infty} e^{-i(k_x x + k_y y - k_z z)} a_\theta(k_x, k_y, k)$$

$$\left(\frac{dk}{dk_z}\right) dk_x dk_y dk_z$$

$$k_z = \sqrt{4k^2 - k_x^2 - k_y^2}$$

$$\frac{dk}{dk_z} = \frac{d}{dk_z}\left(\frac{1}{2}\sqrt{k_x^2 + k_y^2 + k_z^2}\right) = \frac{1}{2}\frac{k_z}{\sqrt{k_x^2 + k_y^2 + k_z^2}}$$

[Math. 11]

$$P(X, Y, Z) = \int_0^{2\pi} \rho(x, y, z, \theta)d\theta \quad (D)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the substantial cone is set to the origin, a direction directed from the origin toward the center of a base of the substantial cone is set to a Z direction, a direction passing through the origin in parallel to the base is set to an X direction, and a direction passing through the origin in parallel to the base and orthogonal to the X direction is set to a Y direction; ρ is a function of permittivity; φ is the reconstruction function; $a_\theta$ is a coefficient; $k_x$, $k_y$, and $k_z$ are respectively x, y and z components of a wave number; k is a time wave number; and θ is a rotation angle with an axis of the substantial cone as a rotation axis.

15. The imaging apparatus according to claim 14, wherein the transmitting antenna element and the receiving antenna element are integrally moved along a line corresponding to a curved generating line of a substantial cone in the target object.

16. The imaging apparatus according to claim 11, wherein the shape indicated by the analysis model is a shape of an asymmetric pyramid, wherein the imaging function is expressed by the following Equation (F) in a case where each of ξ, η, and ζ is a variable satisfying the following Equation (E), and wherein the image reconstruction unit reconstructs the image regarding the internal information of the target object by using a function expressed by the following Equation (G) which is obtained by integrating the imaging function with respect to θ:

[Math. 12]

$$\xi = -k_x\cos\theta + \{k_y\cos\alpha(\theta) + k_z\sin\alpha(\theta)\}\sin\theta \quad (E)$$
$$\eta = -k_x\sin\theta - \{k_y\cos\alpha(\theta) + k_z\sin\alpha(\theta)\}\cos\theta$$
$$\zeta = -k_y\sin\alpha(\theta) + k_z\cos\alpha(\theta)$$
$$k_x = -\xi\cos\theta - \eta\sin\theta$$
$$k_y = (\xi\sin\theta - \eta\cos\theta)\cos\alpha(\theta) - \zeta\sin\alpha(\theta)$$
$$k_z = (\xi\sin\theta - \eta\cos\theta)\sin\alpha(\theta) + \zeta\cos\alpha(\theta)$$

[Math. 13]

$$\rho(x, y, z, \theta) = \frac{1}{(2\pi)^2}\int_{-\infty}^{\infty}\int_{-\infty}^{\infty}\int_{-\infty}^{\infty} e^{i(\xi X+\eta Y+\zeta Z)}\tilde{\phi}_R(k_y, k, \theta)\left(\frac{dk}{dk_z}\right)d\xi d\eta d\zeta \quad (F)$$

$$k = \frac{1}{2}\sqrt{k_x^2 + k_y^2 + k_z^2} = \frac{1}{2}\sqrt{\xi^2 + \eta^2 + \zeta^2}$$

$$\frac{dk}{dk_z} = \frac{k_z}{2\sqrt{k_x^2 + k_y^2 + k_z^2}} = \frac{(\xi\sin\theta - \eta\cos\theta)\sin\alpha + \zeta\cos\alpha}{2\sqrt{\xi^2 + \eta^2 + \zeta^2}}$$

[Math. 14]

$$P(X, Y, Z) = \int_0^{2\pi}\rho(x, y, z, \theta)d\theta \quad (G)$$

here, x is an x coordinate of each of the positions of the transmitting point and the receiving point; y is a y coordinate of each of the positions of the transmitting point and the receiving point; z is a z coordinate of each of the positions of the transmitting point and the receiving point; (X,Y,Z) is a coordinate in a case where a vertex of the pyramid is set to the origin, a direction directed from the origin toward the center of a base of the pyramid is set to a Z direction, a direction passing through the origin in parallel to the base is set to an X direction, and a direction passing through the origin in parallel to the base and orthogonal to the X direction is set to a Y direction; ρ is a function of permittivity; ϕ is the reconstruction function; $\phi_R$ is a function satisfying $\phi(x,y,0,k)\phi_R(y,k)\delta(x)$; $a_\theta$ is a coefficient; $k_x$, $k_y$, and $k_z$ are respectively x, y and z components of a wave number; k is a time wave number; θ is a rotation angle with an axis of the pyramid as a rotation axis; and α is an inclined angle with the Z direction as a reference.

17. The imaging apparatus according to claim 16, wherein the transmitting antenna element and the receiving antenna element are integrally moved along a line corresponding to a generating line of an asymmetric pyramid in the target object.

18. The imaging apparatus according to claim 11, further comprising:
a probe in which the receiving antenna element and the transmitting antenna element are integrally provided,
wherein an electric wave absorbing portion is located between the receiving antenna element and the transmitting antenna element.

19. The imaging apparatus according to claim 11, wherein the wave is a microwave.

20. The imaging apparatus according to claim 11, wherein the wave is a pulse wave or a periodic wave with a predetermined frequency.

* * * * *

UNITED STATES PATENT AND TRADEMARK OFFICE
CERTIFICATE OF CORRECTION

PATENT NO. : 10,586,354 B2
APPLICATION NO. : 15/764091
DATED : March 10, 2020
INVENTOR(S) : Kenjiro Kimura It is certified that error appears in the above-identified patent and that said Letters Patent is hereby corrected as shown below:

In the Specification

Column 17, Line 65, "a point so as to be" should read -- a point ξ so as to be --.

Column 20, Line 46, "T" should read -- ϕ --.

Column 21, Lines 55-59, replace the [Math 28] equation with the following equation:
[Math. 28]

$$(D_z^2 - k_x^2 - k_y^2 + 4k^2)\tilde{\varphi} = 0 \qquad (12)$$

Column 22, Line 48, "($k_x,k_y,k_z$)" should read -- ($k_x,k_y,k$) --.

Column 22, Lines 50-55, replace the [Math 34] equation with the following equation:
[Math. 34]

$$a(k_x, k_y, k) = \tilde{\phi}_R(k_y, k) \qquad (18)$$

Signed and Sealed this
Ninth Day of June, 2020

Andrei Iancu
*Director of the United States Patent and Trademark Office*

Column 23, Lines 16-20, replace the [Math 37] equation with the following equation:

[Math. 37]

$$\tilde{\phi}_R\left(k_{y1}, k_{y2}, k\right)$$

Column 23, Lines 25-35, replace the [Math 39] equation with the following equation:

[Math. 39]

$$\rho(x,y,z,\theta) = \int_{-\infty}^{\infty} \phi(x,y,z,k)\,dk$$

$$= \frac{1}{(2\pi)^2} \int_{-\infty}^{\infty}\int_{-\infty}^{\infty}\int_{-\infty}^{\infty} e^{-i(k_x x + k_y y)} e^{ik_z z} \tilde{\phi}_R(k_y, k, \theta)\left(\frac{dk}{dk_z}\right) dk_x dk_y dk_z \tag{21}$$

Column 25, Lines 1-20, replace the [Math 48] equation with the following equation:

[Math. 48]

$$P(X,Y,Z) = \int_0^{2\pi} \rho(x,y,z,\theta)\,d\theta$$

$$= \frac{1}{(2\pi)^2} \int_0^{2\pi}\int_{-\infty}^{\infty}\int_{-\infty}^{\infty}\int_{-\infty}^{\infty} e^{j(\xi X + \eta Y + \varsigma Z)} \tilde{\phi}_R(k_y, k, \theta)\left(\frac{dk}{dk_z}\right) d\xi\,d\eta\,d\varsigma\,d\theta$$

$$k_y = (\xi \sin\theta - \eta \cos\theta)\cos\alpha - \varsigma \sin\alpha$$

$$k = \frac{1}{2}\sqrt{k_x^2 + k_y^2 + k_z^2} = \frac{1}{2}\sqrt{\xi^2 + \eta^2 + \varsigma^2}$$

$$\frac{dk}{dk_z} = \frac{k_z}{2\sqrt{k_x^2 + k_y^2 + k_z^2}} = \frac{(\xi \sin\theta - \eta \cos\theta)\sin\alpha + \varsigma \cos\alpha}{2\sqrt{\xi^2 + \eta^2 + \varsigma^2}} \tag{30}$$

CERTIFICATE OF CORRECTION (continued)
U.S. Pat. No. 10,586,354 B2

Column 29, Line 26, "a point so as to be" should read -- a point ξ so as to be --.

Column 32, Lines 49-54, replace the [Math 65] equation with the following equation:
[Math. 65]

$$\Phi_I(k_x, y_I, k) = \int_{-\infty}^{\infty} \int_{-\infty}^{\infty} e^{-ikt-ik_x x} \delta(x) \phi_R(y_I, z_I, t) dt dx$$

$$= \int_{-\infty}^{\infty} e^{-ikt} \phi_R(y_I, z_I, t) dt$$

(47).

Column 32, Lines 61-65, replace the [Math 66] equation with the following equation:
[Math. 66]

$$\Psi_I(y_I, k, \theta) = \int_{-\infty}^{\infty} e^{-ikt} \phi_R(y_I, z_I, t) dt$$

(48).

Column 33, Line 35, insert -- If the equation is integrated, the following equation is obtained --.

Column 33, Lines 37-44, replace the [Math 70] equation with the following equation:
[Math. 70]

$$e^{ik_y' y_I} \Psi_I(y_I, k, \theta)$$

$$= \int_{-\infty}^{\infty} \int_{-\infty}^{\infty} \delta(k_x' - k_x) \delta(k_y' - k_y) a_I(k_x, k_y, k) e^{iz_I \sqrt{4k^2 - k_x^2 - k_y^2}} dk_x dk_y$$

$$= a_I(k_x', k_y', k) e^{iz_I \sqrt{4k^2 - k_x'^2 - k_y'^2}}$$

(52).

Column 33, Line 47, "$(k_x,k_y,k_z)$" should read -- $(k_x,k_y,k)$ --.

In the Claims

Claim 6, Column 44, Line 16, "$\phi(x,y,0,k)=\phi(y,k)\delta(x)$" should read -- $\phi(x,y,0,k)=\phi_R(y,k)\delta(x)$ --.

Claim 16, Column 48, Line 9, "$\phi(x,y,0,k)\phi_R(y,k)\delta(x)$" should read -- $\phi(x,y,0,k)=\phi_R(y,k)\delta(x)$ --.